United States Patent
Pozzorini et al.

(10) Patent No.: US 11,830,579 B2
(45) Date of Patent: Nov. 28, 2023

(54) METHODS FOR DETECTING BIALLELIC LOSS OF FUNCTION IN NEXT-GENERATION SEQUENCING GENOMIC DATA

(71) Applicant: SOPHIA GENETICS SA, Saint-Sulpice (CH)

(72) Inventors: Christian Pozzorini, Saint-Sulpice (CH); Zhenyu Xu, Commugny (CH)

(73) Assignee: Sophia Genetics SA, Saint-Sulpice (CH)

( * ) Notice: Subject to any disclaimer, the term of this patent is extended or adjusted under 35 U.S.C. 154(b) by 896 days.

(21) Appl. No.: 16/633,916

(22) PCT Filed: Jul. 24, 2018

(86) PCT No.: PCT/EP2018/070079
§ 371 (c)(1),
(2) Date: Jan. 24, 2020

(87) PCT Pub. No.: WO2019/020652
PCT Pub. Date: Jan. 31, 2019

(65) Prior Publication Data
US 2021/0366570 A1 Nov. 25, 2021

(30) Foreign Application Priority Data
Jul. 25, 2017 (EP) .................... 17183147

(51) Int. Cl.
*G16B 20/20* (2019.01)
*G16B 40/30* (2019.01)
*G16B 20/10* (2019.01)
*C12Q 1/6869* (2018.01)

(52) U.S. Cl.
CPC .......... *G16B 20/20* (2019.02); *C12Q 1/6869* (2013.01); *G16B 20/10* (2019.02); *G16B 40/30* (2019.02)

(58) Field of Classification Search
CPC ........ G16B 20/20; G16B 20/10; G16B 40/30; C12Q 1/6869; C12Q 1/6827
See application file for complete search history.

(56) References Cited

U.S. PATENT DOCUMENTS

| | | | |
|---|---|---|---|
| 2014/0296281 A1 | 10/2014 | Gompel | |
| 2017/0022569 A1 | 1/2017 | Abkevich | |

FOREIGN PATENT DOCUMENTS

| | | |
|---|---|---|
| WO | 2013/076295 | 5/2013 |
| WO | 2014/026096 | 2/2014 |
| WO | 2014/183078 | 11/2014 |
| WO | 2015/070191 | 5/2015 |
| WO | 2015/148776 | 10/2015 |

OTHER PUBLICATIONS

Mafficini A, Simbolo M, Parisi A, Rusev B, Luchini C, Cataldo I, Piazzola E, Sperandio N, Turri G, Franchi M, Tortora G, Bovo C, Lawlor RT, Scarpa A. BRCA somatic and germline mutation detection in paraffin embedded ovarian cancers by next-generation sequencing. Oncotarget 7(2): 1076-1083. (Year: 2016).*

Chen M, Gunel M, Zhao H. SomatiCA: identifying, characterizing and quantifying somatic copy number aberrations from cancer genome sequencing data. PLos One 8(11): e78143. (Year: 2013).*

Su X, Zhang L, Zhang J, Meric-Bernstam F, Weinstein JN. Purity-EST: estimating purity of human tumor samples using next-generation sequencing data. Bioinformatics 28(17): 2265-2266. (Year: 2012).*

Decker B, Karyadi DM, Davis BW, Karlins E, Tillmans LS, Stanford JL, Thibodeau SN, Ostrander EA. Biallelic BRCA2 mutations shape the somatic mutational landscape of aggressive prostate tumors. American Journal of Human Genetics 98(5): 818-829. (Year: 2016).*

Ha G, Roth A, Khattra J, Ho J, Yap D, Prentice LM, Melnyk N, McPherson et al. TITAN: inference of copy number architectures in clonal cell populations from tumor whole-genome sequence data. Genome Research 24: 1881-1893. (Year: 2014).*

International Search Report and Written Opinion of the International Searching Authority for PCT/EP2018/070079.

H. Davies et al., "HRDetect is a predictor of BRCA1 and BRCA2 deficiency based on mutational signatures", Nature Medicine, published online Mar. 13, 2017.

Gray et al., "TumorNext: A comprehensive tumor profiling assay that incorporates high resolution copy number analysis and germline status to improve testing accuracy", Oncotarget. Oct. 18, 2016, 7(42), Published online Sep. 8, 2016. doi: 10. J 8632/oncofmget. 11010, pp. 68206-68228.

(Continued)

*Primary Examiner* — G. Steven Vanni
*Assistant Examiner* — Robert James Kallal
(74) *Attorney, Agent, or Firm* — BOCHNER PLLC; Andrew D. Bochner

(57) ABSTRACT

A genomic data analyzer maybe configured to detect and characterize biallelic genomic alterations for at least one gene in next generation sequencing variant calling information for patient tumor samples characterized by different purity ratios of somatic genomic material. The variant analysis module may compare the observed variant fraction distributions of putative heterozygous germline mutations to the theoretical distributions corresponding to different chromosomal aberration events to detect a combination of genomic alteration events. The variant analysis module maybe used in next-generation-sequencing oncogenomics testing to identify biallelic loss of function on tumor suppressor genes to facilitate the biological understanding and choice of a personalized oncology treatment targeting the analyzed patient tumor solely from next generation sequencing data variant information, without requiring complementary germline analysis or biological assays. The proposed genomic data analyzed may help determine whether PARP inhibitors such as Olaparib are a recommended chemotherapy treatment to target ovarian or breast cancers.

16 Claims, 12 Drawing Sheets

(56) References Cited

OTHER PUBLICATIONS

Dougherty et al., "Biological and clinical evidence for somatic mutations in BRCA1 and BRCA2 as predictive markers for olaparib response in high-grade serous ovarian cancers in the maintenance setting", Oncotarget Advance Publications 2017, published online May 4, 2017.

Maxim Ivanov et al., "Towards standardization of next-generation sequencing of FFPE samples for clinical oncology: intrinsic obstacles and possible solutions", Journal of Translational Medicine, vol. 15, No. 1, Jan. 31, 2017 (Jan. 31, 2017), XP055522113, DOI: 10.1186/s12967-017-1125-8.

B. Evers et al., "Selective Inhibition of BRCA2-Deficient Mammary Tumor Cell Growth by AZD2281 and Cisplatin", Clinical Cancer Research, vol. 14, No. 12, Jun. 15, 2008, XP055522140, ISSN: 1078-0432, DOI: 10.1158/ 1078-0432.CCR-07-4953, pp. 3916-3925.

S. R0ttenberg et al., "High sensitivity of BRCA1-deficient mammary tumors to the PARP inhibitor AZD2281 alone and in combination with platinum drugs", Proceedings of the National Academy of Sciences of the United States of America, vol. 105, No. 44, Nov. 4, 2008 ( Nov. 4, 2008), XP055522138, ISSN: 0027-8424, DOI: 10.1073/pnas.0806092105, pp. 17079-17084.

Mengjie Chen et al., "SomatiCA: Identifying, Characterizing and Quantifying Somatic Copy Number Aberrations from Cancer Genome Sequencing Data", PLOS ONE, vol. 8, No. 11, Nov. 12, 2013, XPO55522049, DOI: 10.1371/ journal.pone.0078143, pp. e78143.

Myriad GmbH: Tumor BRACAnalysis CDx® Technical Specifications Effective Date: Dec. 31, 2014.

Absolute quantification of somatic DNA alterations in human cancer by Scott L Carter et al. dated May 2012.

Integrated Analysis of Germline and Somatic Variants in Ovarian Cancer by Krishna L. Kanchi et al. dated Jul. 2014.

Using next-generation sequencing for high resolution multiplex analysis of copy number variation from nanogram quantities of DNA from formalin-fixed paraffin-embedded specimens by Henry M. Wood et al. dated Jun. 2010.

Analytic Validation: NGS Tumor Genomic Profiling by Julia Elvin dated Mar. 2016.

Tumour testing to detect BRCA mutations dated Apr. 2017.

A Robust Method for Next Generation Sequencing Tumour BRCA1 and BRCA2 Analysis in Formalin Fixed Paraffin Embedded Tissue by Andrew Wallace.

Development of a Comprehensive NGS Workflow for the Analysis of Tumor BRCA1 and BRCA2 Mutations and Large Rearrangements by Zhengwei Dong et al dated Sep. 2015.

Low level somatic variant detection by Sanger sequencing of formalin-fixed paraffin-embedded (FFPE) samples by Arpad Gerstner et al.

A reliable method for the detection of BRCA1 and BRCA2 mutations in fixed tumour tissue utilizing multiplex PCR-based targeted next generation sequencing by Gillian Ellison et al. dated 2015.

\* cited by examiner a)

b)

| Sample | BRCA2 | TP53 | BRCA1 | |
|---|---|---|---|---|
| Sample 1 | | B | | X |
| Sample 2 | B | | C | X |
| Sample 3 | | D | C | X |
| Sample 4 | | D | C | X |
| Sample 5 | | D | E | |
| Sample 6 | | A | A | |
| Sample 7 | | D | A | |
| Sample 8 | | A | | |
| Sample 9 | | D | C | X |
| Sample 10 | | D | | |
| Sample 11 | C | A | | X |
| Sample 12 | | D | | |
| Sample 13 | | C/D | C | X |
| Sample 14 | | A | A | |
| Sample 15 | A | C/D | C/D | X |
| Sample 16 | | A | C | X |
| Sample 17 | | A | | |
| Sample 18 | A | A | | |
| Sample 19 | | C/D | | |
| Sample 20 | | D | | |
| Sample 21 | | A | | |
| Sample 22 | A | A | A | |
| Sample 23 | C | A | | X |
| Sample 24 | | A | A | |
| Sample 25 | C | D | | X |
| Sample 26 | | A | A | |
| Sample 27 | | D | C | X |
| Sample 28 | | A | | X |
| Sample 29 | | A | | |
| Sample 30 | | D | | |
| Sample 31 | | A | C | X |
| Sample 32 | | A | C | X |
| Sample 33 | C | C/D | | X |
| Sample 34 | | A | | X |
| Sample 35 | | B | | |
| Sample 36 | | C/D | | |
| Sample 37 | | D | | X |
| Sample 38 | | C/D | | |
| Sample 39 | | D | | |
| Sample 40 | C | A | | X |
| Sample 41 | C | D | C | X |
| Sample 42 | A | | | |
| Sample 43 | | | | |
| Sample 44 | | | | |
| Sample 45 | | B | | |
| Sample 46 | | D | C/D | X |
| Sample 47 | | D | | |
| Sample 48 | A | A | E | X |
| Sample 49 | | A | C | X |
| Sample 50 | | D | | |
| Sample 51 | | A | | |
| Sample 52 | A | A | | |
| Sample 53 | | A | | |
| Sample 54 | | D | | |
| Sample 55 | | D | | |
| Sample 56 | | | | |
| Sample 57 | | A | | |
| Sample 58 | | C/D | | |
| Sample 59 | A | A | A | |
| Sample 60 | A | A | | |

*Gene Mutation Status*

Fig 8 b)

METHODS FOR DETECTING BIALLELIC LOSS OF FUNCTION IN NEXT-GENERATION SEQUENCING GENOMIC DATA

CROSS-REFERENCE TO RELATED APPLICATIONS

The present application is a U.S. National Stage of International Patent Application No. PCT/EP2018/070079 filed Jul. 24, 2018, which claims priority under 35 U.S.C. § 365 and 119 of Europe Patent Application No. 17183147.2 filed Jul. 25, 2017, the disclosures of which are expressly incorporated by reference herein in their entireties.

FIELD OF THE INVENTION

Methods described herein relate to genomic analysis in general, and more specifically to next generation sequencing applications for detecting and treating cancer.

BACKGROUND OF THE INVENTION

Next-Generation Sequencing

High throughput next-generation sequencing (NGS) or massively parallel sequencing (MPS) technologies have significantly decreased the cost of DNA sequencing in the past decade. NGS has broad application in biology and dramatically changed the way of research or diagnosis methodologies. For example, RNA expression profiling or DNA sequencing can only be conducted with a few numbers of genes with traditional methods, such as quantitative PCR or Sanger sequencing. Even with microarrays, profiling the gene expression or identifying the mutation at the whole genome level can only be implemented for organisms whose genome size is relatively small. With NGS technology, RNA profiling or whole genome sequencing has become a routine practice now in biological research. On the other hand, due to the high throughput of NGS, multiplexed methods have been developed not just to sequence more regions but also to sequence more samples. Compared to the traditional Sanger sequencing technology, NGS enables the detection of mutation for much more samples in different genes in parallel. Due to its superiorities over traditional sequencing method, NGS sequencers are now replacing Sanger in routine diagnosis. In particular, genomic variations of individuals (germline) or of cancerous tissues (somatic) can now be routinely analyzed for a number of medical applications ranging from genetic disease diagnostic to pharmacogenomics fine-tuning of medication in precision medicine practice. NGS consists in processing multiple fragmented DNA sequence reads, typically short ones (less than 300 nucleotide base pairs). The resulting reads can then be compared to a reference genome by means of a number of bioinformatics methods, to identify small variants such as Single Nucleotide Polymorphisms (SNP) corresponding to a single nucleotide substitution, as well as short insertions and deletions (INDEL) of nucleotides in the DNA sequence compared to its reference.

Tumor Sequencing

In some pathologies, a specific gene variant has been associated with the illness, such as for instance the BRCA1, BRCA2 and TP53 tumor suppressor gene variants in certain forms of hereditary breast and ovarian cancers. Beyond inherent germline mutations, cancer cells often carry somatic gross chromosomal aberrations such as copy number variations, causing duplications or hemizygous deletions of certain alleles or genomic regions. Some of these variants may thus cause a loss of function of the tumor suppressor mechanisms, such as the homologous repair (HR) function, thus making the cancer more aggressive. Identifying those variants is of key importance in recent advances of personalized cancer medication, as the resulting tumors have been shown particularly responsive to certain therapeutic compounds such as the PARP (poly ADP-ribose polymerase) inhibitors. An example of a PARP inhibitor that exploits tumor DNA damage response (DDR) pathway deficiencies to selectively destroy cancer cells is olaparib, currently approved in the US and in Europe for certain categories of ovarian cancers associated with BRCA gene mutations. There is therefore a need to better characterize those genomic variants from somatic tumor samples.

Recent research has shown that beyond well-studied germline variants, somatic variants such as substitutions, insertions, deletions and rearrangement patterns can cause BRCAness (BRCA1 or BRCA2 loss of function) with different mutation profiles. In "HRDetect is a predictor of BRCA1 and BRCA2 deficiency based on mutational signatures", H. Davies et al., *Nature Medicine*, published online Mar. 13, 2017, Whole Genome Sequencing (WGS) is shown as a possible method to detect those loss-of-function mutation profiles, with a 98.7% sensitivity, from mutational signatures in the whole genome sequencing data. In contrast to WGS, the authors report that when only Whole Exome Sequencing is applied, the sensitivity significantly drops, between 46.8% and 73% depending on specific adaptations of the bioinformatics algorithms.

In "*TumorNext: A comprehensive tumor profiling assay that incorporates high resolution copy number analysis and germline status to improve testing accuracy*", Oncotarget. 2016 Oct. 18; 7(42): 68206-68228, Published online 2016 Sep. 8. doi: 10.18632/oncotarget.11910, Gray et al. describe a probe-based target enrichment assay coupled with Next Generation Sequencing (NGS) for deletion of CNVs (Copy Number Variants) and SNPs, including hemizygous status. This method assumes independent germline status testing from blood samples in addition to the somatic sample analysis. To provide enough sensitivity and specificity, it assumes a coverage of at least 500× by the dedicated probe-based assay, as well as sufficient DNA input from the FFPE samples. These requirements restrict its cost-effective routine use.

In "*Biological and clinical evidence for somatic mutations in BRCA1 and BRCA2 as predictive markers for olaparib response in high-grade serous ovarian cancers in the maintenance setting*", Oncotarget Advance Publications 2017, published online May 4, 2017, Dougherty et al. present preliminary clinical evidence that olaparib may benefit to ovarian cancer patients with somatic BRCA1/2 mutations like it benefits to those with germline mutations. Moreover, they observe that somatic mutations had more than 80% biallelic inactivation frequency and were predominantly clonal, suggesting that BRCA1/2 loss occurs early in the development of these cancers. As explained by the authors, the conventional germline BRCA1 and BRCA2 mutational status by PCR and Sanger sequencing does not perform cost effectively in somatic applications. In particular it cannot accurately detect the low allele frequencies encountered in small amounts of low-quality DNA sequenced from FFPE tissue with variable tumour cellularity.

There is therefore a need for dedicated NGS assays and methods development, which can be easily and cost-effectively deployed in automated NGS setups for routine diagnosis solely from tumour samples, without requiring manual data analysis and/or complementary biological assays such as germline (blood sample) genomic analysis.

Targeted Enrichment

Rather than sequencing the whole genome (WGS) from an individual sample, the genomic analysis can focus on the genome region associated with the illness, by targeting, with a set of region-specific DNA primers or probes, and enriching or amplifying, for instance with PCR (Polymerase Chain Reaction), the biological DNA sample specifically for sub-regions corresponding to the gene along the DNA strand. A number of next generation sequencing assays have now been developed along those principles as ready-to-use biological kits, such as for instance the Multiplicom MASTR™ (Dx (http://www.multiplicom.com/product/brca-mastr-dx) assay kits to facilitate DNA based diagnostics with next generation sequencers, such as for instance the Illumina MiSeq® sequencer, in medical research and clinical practice.

Target enrichment may be achieved from a small sample of DNA by means of probe-based hybridization (on arrays or in-solution) or highly multiplexed PCR-based targeted exon enrichment, so that both the gene coverage/read depth and the amplification specificity (amplifying the right region, as measured by further alignment to the desired target regions) are maximized. Examples of commercially available target enrichment systems include Agilent SureSelect™ Target Enrichment System, Roche NimbleGen SeqCap EZ, Illumina Nextera Rapid Capture, Agilent Haploplex™° and Multiplicom MASTR™.

In order to maximize the use of the massively-parallel processing NGS sequencer, a number of samples are multiplexed in the targeted NGS experiment—a pool of 48 or more target enrichment samples can thus be simultaneously input to the Illumina MiSeq sequencer for instance. Raw sequencing data out of the NGS sequencer may then be analyzed to identify specific subsequences, for instance by alignment to a reference genome. As a result, the amplification may produce more than a thousand reads for a given amplicon in a patient sample.

Next Generation Sequencing Workflow Automation

Next Generation Sequencing (NGS) enables in particular to detect and report small changes in the DNA sequence, such as single nucleotide polymorphisms (SNPs), insertions or deletions (INDELs), as compared to the reference genome, through bioinformatics methods such as sequencing read alignment, variant calling, and variant annotation. NGS workflows refer to the configuration and combination of such methods into an end-to-end genomic analysis application. In genomic research practice, NGS workflows are often manually setup and optimized using for instance dedicated scripts on a UNIX operating system, dedicated platforms including a graphical pipeline representation such as the Galaxy project, and/or a combination thereof. As clinical practice develops, NGS workflows may no longer be experimentally setup on a case-per-case basis, but rather integrated in SaaS (Software as a Service), PaaS (Platform as a Service) or IaaS (Infrastructure as a Service) offerings by third party providers. In that context, further automation of the NGS workflows is key to facilitate the routine integration of those services into the clinical practice.

While next generation sequencing methods have been shown more efficient than traditional Sanger sequencing in the detection of SNPs and INDELs, their specificity (rate of true positive detection for a given genomic variant) and sensitivity (rate of true negative exclusion for a given genomic variant) may still be further improved in clinical practice. The specificity and sensitivity of NGS genomic analysis may be affected by a number of factors:

Biases introduced by the sequencing technology, for instance due to:
  Length of the reads relative to the length of the fragments;
  Too small number of reads (read depth);
  Errors or low quality bases introduced during sequencing;
  Inherent difficulties in counting homopolymer stretches, in particular with pyrosequencing (as in Roche 454 platforms) or semiconductor sequencing (as in Ion Torrent platforms), resulting in insertion and deletion errors;

Biases introduced by the DNA enrichment technology, for instance due to:
  Primers or probes non-specific binding, for instance due to storing the assay at a low temperature for too long, or due to too small amount of DNA in the sample;
  Introduction of sequence errors caused by imperfect PCR amplification and cycling, for instance due to temperature changes;
  Suboptimal design of the probes or primers. For example, mutations may fall within the regions of the probes or primers;
  Enrichment method limitations. For instance, long deletion may span the amplified region;
  Cross-contamination of data sets, read loss and decreased read quality due to fragment tagging with barcodes, adapters and various pre-defined sequence tags;
  Chimeric reads in long-insert pair-ended reading.

Biases introduced by the sample itself, for instance due to:
  Somatic features, in particular in cancer diagnosis based on formalin-fixed, paraffin-embedded (FFPE) tumor samples sequencing, as the FFPE tumor material is often small, with low quality DNA material resulting in lower coverage depth by the next generation sequencer; moreover, tumor samples typically contain heterogeneous DNA from a mixture of somatic cells with diverse DNA alterations and normal cells with germline DNA variants, which challenges their reading (low resolution coverage signal), interpretation (variant calling), phasing (identification of which alleles carry which variant, for instance to discriminate between monoallelic versus biallelic genomic alterations of interest to certain precision medicine applications) and prioritization (identification of most likely variants with pathological impact).
  The type of biological sample, e.g. blood, urine, saliva, and associated sample preparation issues, for instance causing degradation of DNA, contamination with alien DNA, or too low DNA input.

Biases introduced by the genomic data structure of certain regions specifically, for instance due to:
  High ratio of GC content in the region of interest;
  Presence of homopolymers and/or heteropolymers, that is partial genomic sequence repetitions of one or more nucleotides in certain regions, causing ambiguities in initial alignment, and possibly inherent sequencing errors in particular with the Roche 454 and Ion Torrent sequencer technologies;
  Presence of homologous and low-complexity regions;
  Presence of non-functional pseudogenes that may be confused with functional genes, in particular in high-repeat genomic regions of the human genome when the DNA fragments are not long enough compared to the read length;

Presence of cancer-specific Copy Number Variants (CNVs), such as deletions or duplications. Those DNA rearrangements may be very large, for instance, in the case of ovarian cancer cells, somatic whole-gene CNVs are very frequent, which disturbs any statistical analysis based on the coverage signal alone.

Due the above biases, the NGS data is particularly noisy and often requires complementary experiments on a case per case basis to detect variants of clinical relevance at sufficient sensitivity and specificity. As example in breast and ovarian cancer genomic analysis practice, most BRCA test service providers for germline mutations require complementary analysis such as Sanger sequencing or MLPA analysis of CNV mutations in parallel with the NGS genomic analysis of SNP and INDEL variants. This approach is costly and does not scale well as more and more tests have to be conducted in daily operation by a single multi-purpose genomic analysis platform. Patent application PCT/EP2016/078113 addresses this limitation by describing a method to detect copy-number values (CNV) from a pool of DNA samples enriched with a target enrichment technology, based on a between-samples normalization of the genomic coverage signal, which can be applied by an NGS genomic data analyzer module in parallel with SNP/INDEL detection from the same target enrichment assay and next-generation sequencing experiment instead of requiring separate NGS and MLPA experiments and analyzers. This method however assumes sufficient homogeneity in the input DNA and resulting genomic alignment coverage data for its statistical model hypotheses to be valid. That is usually the case in germline cell analysis with good laboratory practice, but it cannot always reliably infer the somatic whole gene CNVs that may be present in tumor cell DNA from the coverage signal alone, especially when only low resolution coverage depth is available.

Still, recent works in somatic NGS analysis have highlighted the challenge of detecting large rearrangements as genomic alterations of pathologic relevance out from the tumor sample itself. For instance, Ellison et al. *"A reliable method for the detection of BRCA1 and BRAC2 mutations in fixed tumor tissue utilising multiplex PCR-based targeted next generation sequencing"*, BMC Clinical Pathology (2015) 15:5 indicates that while MLPA may in theory be used to detect large rearrangements in FFPE tissue, in practice it raises data analysis challenges to cope with genomic instability in the tumor genome that may affect the control probes as well as to detect low level signals associated with somatic mutations.

The Tumor BRACAnalysis CDx commercial test from Myriad GmbH (Technical Specifications—Dec. 31, 2014) analyses copy number abnormalities indicative of deletion or duplication rearrangements based on the coverage signal (number of next generation sequencing reads that map to each nucleotide, normalized to the run median depth of coverage of the same nucleotide) and is therefore subject to certain limitations, in particular it cannot reliably detect certain specific insertions, inversions and regulatory mutations, the detection of large rearrangement deletions and duplications is subject to the quality of the FFPE sample, and not all of them can be assessed. Some duplications are reported as variants of uncertain significance, which have to be further analyzed manually.

Moreover, the current state of the art in automated CNV variant calling assumes a high-resolution depth of coverage analysis, as quoted for instance in Kang et al. *Design and validation of a next generation sequencing assay for hereditary BRCA1 and BRCA2 mutation testing*, PeerJ 4:e2162.

There is currently no known efficient genomic analysis method to automatically and reliably detect and categorize the biallelic loss of function status of tumor suppressor genes by analyzing FFPE tumor samples solely from next generation sequencing variant information without complementary biological or manual analyses.

There is therefore a need for improved genomic analysis methods to efficiently, automatically and reliably detect and categorize genomic alterations from FFPE tumor DNA samples to better determine the biallelic loss of function status of target genes in each individual sample, regardless of whether this loss of function is caused by germline or somatic mutations or chromosomal aberrations or a combination thereof.

BRIEF SUMMARY

It is proposed a method for identifying the presence of a chromosomal aberration in the tumor sample cells in at least one gene from the next generation sequencing data analysis of a pool of patient tumor samples, with a variant classification data processor module, in which a combination of at least two genomic alterations have caused its biallelic loss of function, the method comprising:

acquiring a variant calling information of the next generation sequencing of multiple patient tumor samples, the variant calling information comprising for each patient a list of SNPs and INDELs genomic variants in at least two genes to be analyzed;

selecting, in the list of genomic variants, a set of putative germline heterozygous SNPs by comparing the list of genomic variants to a reference human genome variant database;

for each possible value sample purity value p, a sample purity p being a ratio of somatic DNA material in the overall FFPE sample, fitting a mixture model to the observed variant fraction distribution of said set in the variant calling data, the modeled variant fraction distribution values being calculated as a function of the sample purity p;

inferring an optimal sample purity $p_{optimal}$ as the possible sample purity p for which the mixture model best fits the observed variant fraction distribution of said set;

for each gene to be analyzed:
  selecting, in the plurality of putative germline heterozygous SNPs, a subset of putative germline heterozygous SNPs located in the gene to be analyzed,
  inferring the presence of a chromosomal aberration in the tumor sample cells by comparing, on at least said subset, the observed variant fraction distribution with the predicted variant fraction distribution for each possible chromosomal aberration, the predicted variant fraction distribution values being calculated as a function of the optimal sample purity $p_{optimal}$.

The variant fraction of each putative germline heterozygous SNP may be compensated for capture-biases, by inferring and compensating the average loss a in capture efficiency due to the presence of a SNP in the tumor samples as the value a for which the compensated variant fraction distribution of all putative germline heterozygous SNP across all samples is maximally symmetric around 50%.

Possible chromosomal aberration in the tumor sample cells may comprise copy-neutral loss-of-heterozygosity, the deletion or the duplication of one allele.

The mixture model may be fitted to the data by minimizing a cost function based on the root mean squared error (RMSE) between the observed and the theoretical variant fraction expected for the most likely chromosomal aberration. Inferring chromosomal aberrations may then comprise minimizing the root mean squared error (RMSE) between the observed variant fraction and the theoretical variant fractions expected for a plurality of chromosomal aberrations.

A mixture model with mixture components corresponding to the different possible chromosomal aberrations using the Expectation-Maximization algorithm or using a Markov-Chain Monte-Carlo sampling algorithm may also be fitted to the data to estimate the sample purity. Inferring the gene chromosomal aberrations may then comprise applying Mixture Model Classifiers.

The method may further comprise detecting germline copy number variants (CNVs) in accordance with a Hidden Markov Model.

The method may further comprise reporting to the end user whether the detected alterations are biallelic, for each gene in each sequenced patient tumor sample.

A least one of the genes to be analyzed may be a tumor suppressor gene, such as for instance one of ATM, CHEK1, CHEK2, BARD1, BRCA1, BRCA2, BRIP1, RAD51C, RAD51D, FAM175A, MRE11A, NBN, PALB2, TP53, APC, DCC, DF1, NF2, PTEN, Rb, VHL, WT1, PP2A, LKB1, or INK4a/ARF.

The proposed methods to detect genomic alterations may also be used for determining if cancer or precancerous lesions or benign tumours in a patient will be responsive to treatment with a PARP inhibitor, comprising:
  obtaining samples of the cancer cells, the precancerous cells or the benign tumour cells from the patient,
  sequencing the sample cells as part of a multiplex targeted next generation sequencing assay;
  analysing, with a genomic data analyser, the next generation sequencing data to identify variant calling information;
  detecting, with the proposed method, genomic alterations in BRCA1 and BRCA2 genes from the variant calling information, and
  if the patient sample cells carry a biallelic genomic alteration in the BRCA1 gene or in the BRCA2 gene, then determining that the patient cancer will respond to treatment with the PARP inhibitor.

The PARP inhibitor may be olaparib.

The proposed methods may be used to treat cancer in a patient, by determining if cancer or precancerous lesions or benign tumors in a patient will be responsive to treatment with a PARP inhibitor using the proposed methods, and treating the cancer in the patient with the PARP inhibitor if the cancer or precancerous lesions or benign tumours in a patient have been determined responsive to treatment with a PARP inhibitor.

DETAILED DESCRIPTION

Next Generation Sequencing Analysis System

Figure 1:
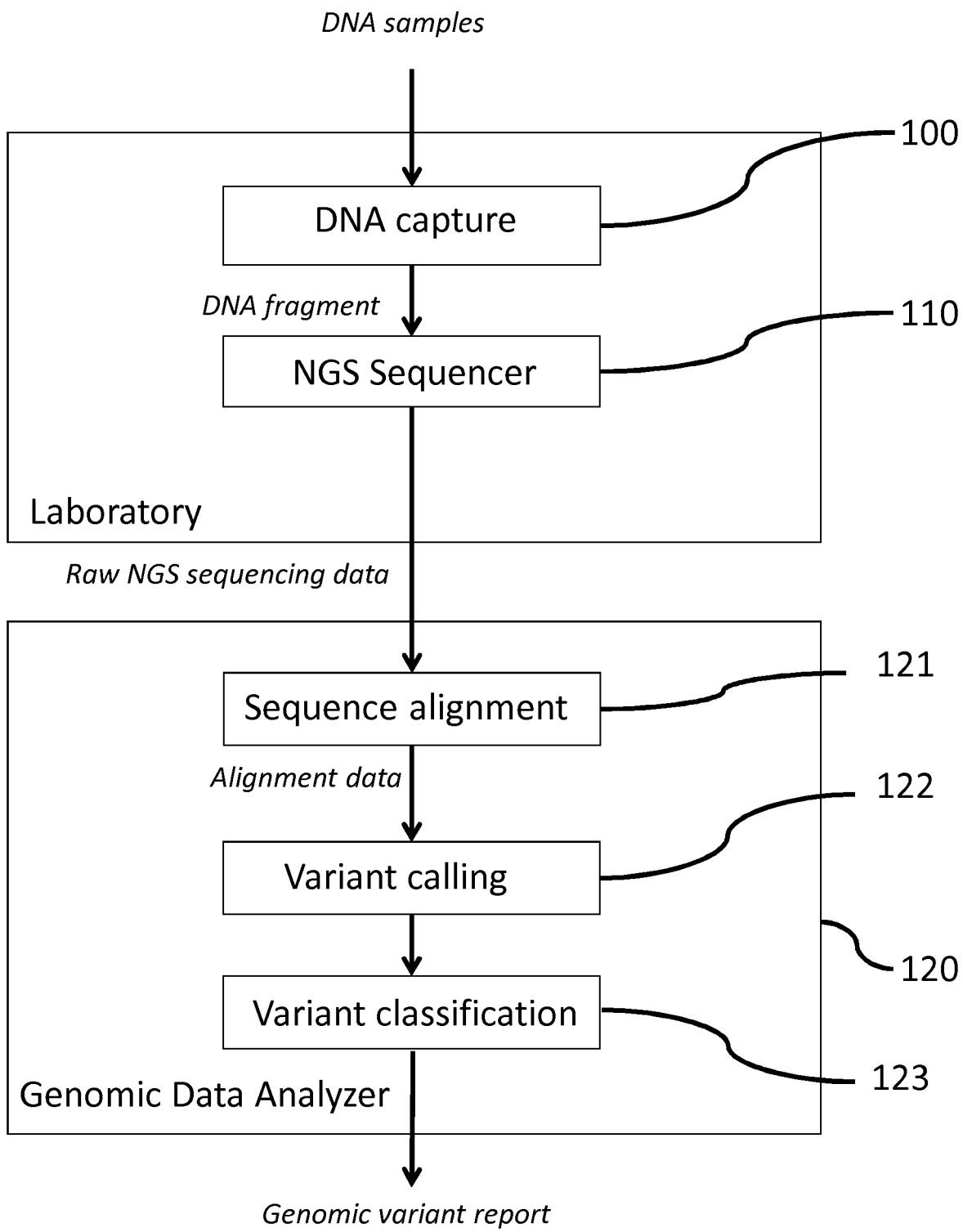
FIG. 1 represents a prior art next generation sequencing system.

FIG. 1 shows an exemplary genomic analysis system comprising a DNA enrichment assay 100, a next generation sequencer 110 and a genomic data analyzer 120.

In a NGS laboratory, a pool of DNA samples is processed by the DNA enrichment assay 100 to generate a library of pooled amplicons (for amplicon-based enrichment) or fragments (for probe-based enrichment) as DNA fragments input to the next generation sequencer 110, each set of amplicons/fragments corresponding to a different sample. The number of amplicons/fragments is application dependent. In some genomic analysis experiments, target enrichment may require 150 primers to enrich 75 different regions to be targeted out of the sample genome, resulting in a set of 75 amplicons for each sample. The number of samples may also be adapted to the next-generation sequencing sequencer 110 parallel processing capability, for instance 48 samples in the form of a library of pooled amplicons may be sequenced in parallel by an Illumina MiSeq sequencer. Other NGS sequencer technologies may be used, such as for instance the Roche 454™ GS Junior or GS FLX, Illumina MiSeq®, or Life Technologies Ion PGM™ sequencers.

The next-generation sequencer 110 analyses the input samples and generates sequence reads in a computer-readable file format representing raw NGS sequencing data. Depending on the NGS technology, one or more files may be output by the NGS sequencer 110. In some embodiments, for instance with Illumina sequencers, the FASTQ file format may be used with two different files for forward and reverse reads or as a single joined file. This text file typically starts with a sequence header marked by a '@' start character, followed by one line of sequence information represented as a string of 'A', 'T', 'C', 'G' nucleotide characters, then by a quality header marked by a '+' start character, followed by one line of quality metrics, one quality score matching each nucleotide read. The format for the quality metrics for each nucleotide in the sequence information string may depend on the sequencer. Some legacy sequencers output the raw sequencing data in the SFF (Standard Flowgram Format) binary file format, which comprises an informative header and the read data. Other embodiments are also possible, for instance some legacy Roche sequencers output multiple FASTQ files for a single patient analysis, while other sequencers, for instance the Ion Torrent PGM sequencers, have migrated to the compressed unmapped BAM file format, as may be recognized from the .basecaller.bam file extension. As known to those skilled in the art of communication systems, the laboratory operates a computing infrastructure to store the resulting raw NGS sequencing data file in a laboratory biobank. The laboratory computing infrastructure connects, with authentication credentials, through a communication network, to the genomic data analyzer 120 and transmits a genomic analysis request comprising the raw NGS sequencing file to the genomic data analyzer 120.

The genomic data analyzer 120 computer system (also "system" herein) 120 is programmed or otherwise configured to implement different genomic data analysis methods, such as receiving and/or combining sequencing data and/or annotating sequencing data.

The genomic data analyzer 120 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. Examples of genomic data analyzer computing systems, environments, and/or configurations include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and the like. In some embodiments, the computer system may comprise one or more computer servers, which are operational with numerous other general purpose or special purpose computing systems and may enable distributed computing, such as cloud computing, for instance in a genomic data farm. In some embodiments, the genomic data analyzer 120 may be integrated into a massively parallel system. In some embodiments, the genomic data analyzer 120 may be directly integrated into a next generation sequencing system.

The genomic data analyzer 120 computer system may be adapted in the general context of computer system-executable instructions, such as program modules, being executed by a computer system. Generally, program modules may include routines, programs, objects, components, logic, data structures, and so on that perform particular tasks or implement particular abstract data types. As is well known to those skilled in the art of computer programming, program modules may use native operating system and/or file system functions, standalone applications; browser or application plugins, applets, etc.; commercial or open source libraries and/or library tools as may be programmed in Python, Biopython, C/C++, or other programming languages; custom scripts, such as Perl or Bioperl scripts.

Instructions may be executed in distributed cloud computing environments where tasks are performed by remote processing devices that are linked through a communications network. In a distributed cloud-computing environment, program modules may be located in both local and remote computer system storage media including memory storage devices.

As illustrated on FIG. 1, the genomic data analyzer 120 may comprise a sequence alignment module 121, which compares the raw NGS sequencing data to a reference genome. The sequence alignment module 121 may be configured to execute different alignment algorithms. Standard raw data alignment algorithms such as Bowtie2 or BWA that have been optimized for fast processing of numerous genomic data sequencing reads may be used, but other embodiments are also possible. The alignment results may be represented as one or several files in BAM or SAM format, as known to those skilled in the bioinformatics art, but other formats may also be used, for instance compressed formats or formats optimized for order-preserving encryption, depending on the genomic data analyzer 120 requirements for storage optimization and/or genomic data privacy enforcement.

The resulting alignment data may be further filtered and analyzed by a variant calling module 122 to retrieve variant information such as SNP and INDEL polymorphisms. The variant calling module 122 may be configured to execute different variant calling algorithms. The resulting detected variant information may then be output by the genomic data analyzer module 120 as a genomic variant report for further processing by the end user, for instance with a visualization tool, and/or by a further variant annotation processing module (not represented).

The genomic data analyzer 120 may be adapted to automatically detect, with a processor, a set of characteristics that uniquely determine the input sequencing data and corresponding genetic context, the DNA enrichment context such as the sample type or laboratory process characteristics, the DNA enrichment technology such as the targeted enrichment target kit or capture probe assay characteristics, and/or the NGS sequencing technology. As will be apparent to those skilled in the art of next generation sequencing, these experimental characteristics may cause specific biases in the sequence alignment and/or the variant calling results.

The proposed genomic data analyzer system 120 may thus serve next generation sequencing genomic analysis requests from different labs that are independently operating different sequencer technologies and different DNA enrichment technologies on different samples for different genes. The proposed genomic data analyzer system 120 may automatically detect a set of characteristics from the input data and requests received from the laboratory and may adapt the configuration of the sequence alignment module 121 and the variant calling module 122 accordingly, without requiring a time consuming and costly manual setup to minimize the data biases possibly induced by each different biological workflow. As will be apparent to those skilled in the art, there may be dozens or even hundreds of different clinical laboratory setups for multiple sourcing laboratories operating with the same genomic analyzer 120, and this number and diversity is likely to further increase with the deployment of additional technologies and assays as the NGS-based personalized medicine clinical practice develops.

Depending on the detected genomic experiment characteristics, the genomic data analyzer 120 may configure the sequence alignment module 121 to operate additional data processing steps and/or use different sets of configuration parameters such that the data biases caused by the genomic experiment characteristics are minimized.

Depending on the detected input characteristics, the genomic data analyzer may further configure the variant calling module 122 to operate additional data processing steps and/or use different sets of configuration parameters such that the data biases caused by the genomic experiment characteristics are minimized.

Depending on the results of the initial sequence alignment by the sequence alignment module 121, the genomic data analyzer 120 may be further adapted to identify next generation sequencing data alignment biases that become apparent when analyzing the alignment data. The genomic data analyzer may accordingly configure the sequence alignment module 121 to execute an additional step of re-alignment of the raw NGS sequencing data. This re-alignment may be constrained by additional parameters as may be determined from the initial alignment results. In a possible embodiment, the re-alignment is applied specifically on a sub-region of the genomic sequence. The resulting re-alignment data may be further filtered and analyzed by the variant calling module 122 to output a more relevant genomic variant report with increased sensitivity and specificity for variant detection.

Depending on the results of the variant calling by the variant calling module 122, the genomic data analyzer 120 may be further adapted to identify variant calling biases that become apparent when calling variants on the alignment data. The genomic data analyzer may accordingly configure the variant calling module 122 to execute an additional step of re-calling variants on all or part of the alignment data. This refined variant calling step may be constrained by additional parameters as may be determined from the former alignment and/or re-alignment and/or variant calling results. In a possible embodiment, variants are specifically called on a subset of the aligned genomic data. The resulting refined variant calling data may be further combined with the standard variant calling results by the variant calling module 122 to output a more relevant genomic variant calling information report with increased sensitivity and specificity for variant detection. In a possible embodiment, some variant calling results may be excluded from the genomic variant report as identified possibly biased by the variant calling module 122, so that a more relevant genomic variant report is generated by the genomic data analyzer 120 with increased sensitivity and specificity for variant detection.

As will be apparent to those skilled in the art of bioinformatics, the variant calling information reported by the variant calling module 122 may be a data file in the VCF format, comprising a list of genomic variants and the associated read depth coverage information. The variant fraction of each genomic variant in the next generation sequencing data can be derived with standard bioinformatics tools such as vcftools. Other embodiments are also possible, for instance the list of called variants, the variant fraction information and/or the coverage information may be acquired by the genomic data analyzer 120 from different file formats.

As will be apparent to those skilled in the art of personalized medicine, the variant calling information is quite complex to interpret and currently requires a good understanding of the underlying methods and format specifics. In order to facilitate the interpretation of the data by non-bioinformatician experts such as biologists and doctors, a variant classification module 123 may further analyze, annotate, categorize and/or prioritize the variant calling information to report to the end user for each tumor suppressor gene a combination of SNPs, INDELs and/or CNV variants which potentially results in a pathogenic loss of function for the tumor suppressor gene. This report may then facilitate the oncogenomics diagnosis of the cancer origin. This report may also facilitate the selection of a medical treatment specifically targeting the analyzed tumor, such as for instance the use of PARP inhibitors in certain BRCA1 and/or BRCA2 loss of function mutations.

In the case of a somatic FFPE sample analysis, the variant classification module 123 may report germline and somatic alterations, for instance SNPs, INDELs, as well as chromosomal aberrations such as allelic imbalance (AI), loss of heterozygosity (LOH), as copy number variations such as aberrations (CNA), gain (CVG) or decrease (CND) as may be caused by large deletions or duplications of an allele genomic region.

In a possible embodiment, in the case of a somatic FFPE sample, the variant classification module 123 may identify that the genome of germline cells is heterozygous for certain variants, and may report separately the variant fraction of different alteration events in cancer cells such as a copy-neutral loss of function, a large deletion resulting in a lower copy number for this variant, or a large duplication resulting in a larger copy number for this variant. The variant classification module 123 may thus identify, categorize and prioritize, in terms of loss-of-function, the combination of different genomic alterations such as germline and somatic alteration variants and chromosomal aberrations.

As will be apparent to those skilled in the art, this bioinformatics method then significantly facilitates detailed understanding of the cancer cells genomic alterations and the adaptation of a personalized medicine treatment to the specifics of the inferred cancer cell biology for the patient.

Exemplary End-to-End Automated Next Generation Sequencing Analysis Workflow

Figure 2:
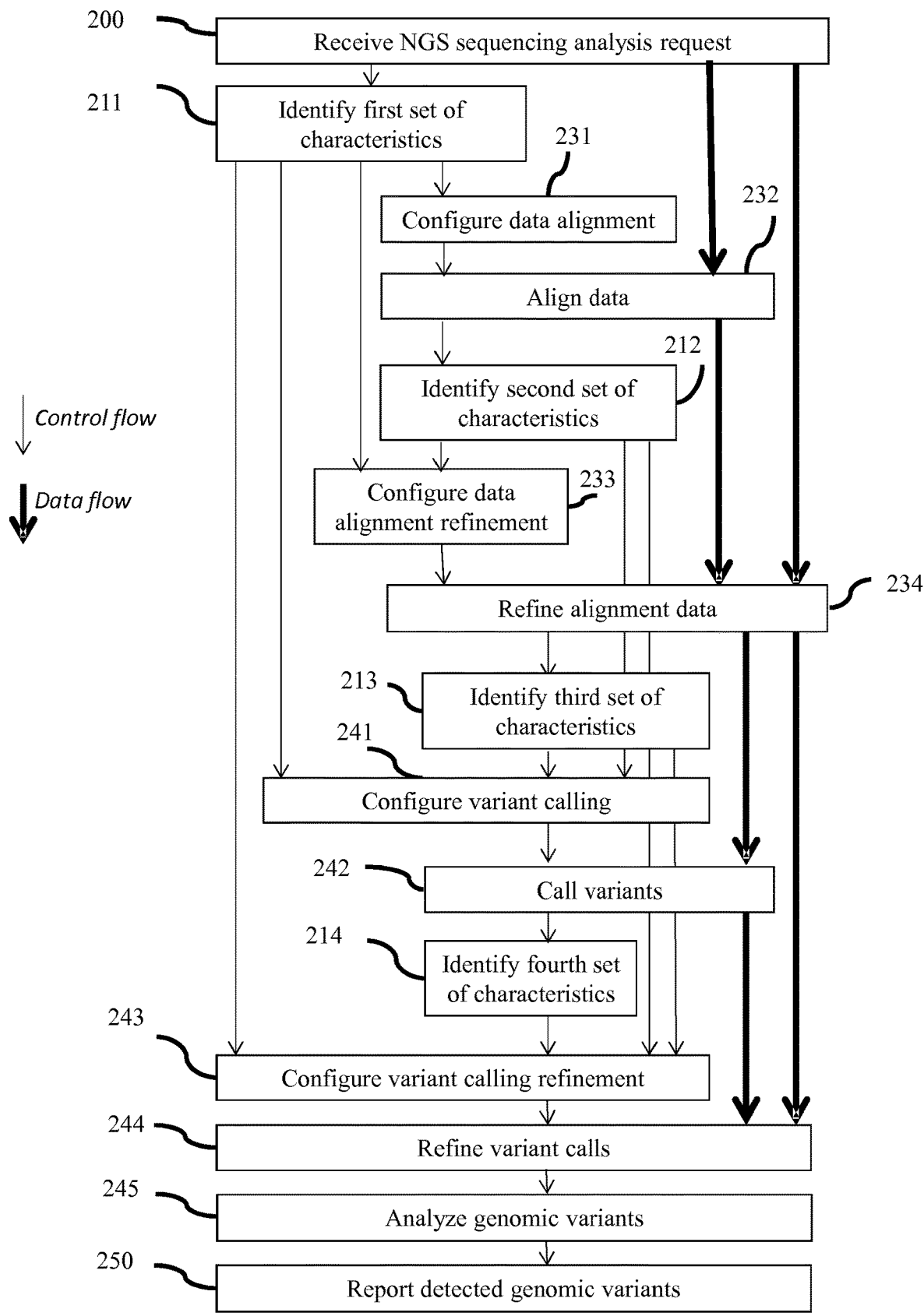
FIG. 2 shows an overall flowchart of a fully automated next generation sequencing genomic analysis workflow.

FIG. 2 shows accordingly a possible genomic analysis workflow for the genomic data analyzer 120, comprising:
- receiving 200 a next generation sequencing analysis request;
- identifying 211 a first set of characteristics associated with the next generation sequencing analysis request, the first set of characteristics comprising at least a target enrichment technology identifier, a sequencing technology identifier, and a genomic context identifier;
- configuring 231 a data alignment module 121 to align the input sequencing data in accordance with at least one characteristic of the first set of characteristics;
- aligning 232, with the configured data alignment module 121, the input sequencing data to a genomic sequence, and reporting the alignment data into a raw alignment data file;
- identifying 212 a second set of characteristics associated with the alignment data from the raw alignment data file, the second set of characteristics comprising at least a data alignment pattern identifier;
- configuring 233 the data alignment module 121 to refine at least one subset of the input sequencing data in accordance with at least one characteristic of the first set of characteristics and at least one characteristic of the second set of characteristics;
- refining 234, with the configured data alignment module 121, the subset of the input sequencing data to produce a refined alignment data file;
- identifying 213 a third set of characteristics associated with the re-alignment data from the refined alignment data file, the third set of characteristics comprising at least a genomic context identifier;
- configuring 241 a variant calling module 122 to detect variants associated with the refined alignment data in accordance with at least one characteristic of the first set of characteristics, at least one characteristic of the second set of characteristics, and at least one characteristic of the third set of characteristics;

detecting 242 a first set of genomic variants, with the configured variant calling module 122, in the refined alignment data;

identifying 214 a fourth set of characteristics associated with the detected genomic variants, the fourth set of characteristics comprising at least a variant calling refinement identifier;

configuring 243 the variant calling module 122 to detect variants associated with the refined alignment data in accordance with at least one characteristic of the first set of characteristics, at least one characteristic of the second set of characteristics, at least one characteristic of the third set of characteristics and at least one characteristic of the fourth set of characteristics;

detecting 244 refined genomic variants, with the configured variant calling module 122, in the refined alignment data and the detected genomic variants, to produce a refined set of genomic variants;

analyzing 245 genomic variants of likely pathogenicity;

reporting 250 the analyzed set of genomic variants.

An exemplary embodiment of the proposed refined variant calling analysis method 245 will now be described in more detail with the example of genomic analysis of ovarian cancer samples, but as will be apparent to those skilled in the art of bioinformatics, the proposed embodiments are not specific to ovarian cancer samples and may similarly apply to other types of cancer tumors genomic analysis.

The fully automated genomic data analysis workflow of FIG. 2 operates on genomic data sourced from at least one next generation sequencing laboratory. The genomic data analyzer 120 receives 200 an NGS sequencing analysis request from the laboratory, comprising raw sequencing data. The genomic data analyzer 120 configures 231 the data alignment module 121 to execute 232 a first raw data alignment. As will be apparent to those skilled in the art of bioinformatics, the data alignment module 121 may first execute 232 pre-processing steps such as removing the assay specific adapters from the reads and/or merging pair-ended raw sequencing data files into a single merged file. The data alignment module 121 aligns 232 the raw sequencing data short reads to a reference genomic sequence such as the reference human genome (hg19), with a raw data alignment algorithm as known to those skilled in the art of bioinformatics, to produce a data alignment file. Standard algorithms such as Bowtie2 or BWA that have been optimized for fast processing of numerous genomic data sequencing reads may be used, but other embodiments are also possible. The resulting data alignment file may be represented as one or several files in BAM or SAM format, but other embodiments are also possible, in particular the data alignment module 121 may also execute 232 post-processing steps such as compressing and/or encrypting the alignment data, for instance with an order-preserving encryption scheme, depending on the genomic data analyzer 120 requirements for storage optimization and/or genomic data privacy enforcement along the genomic analysis workflow processing.

The genomic data analyzer 120 may also further detect 212 the presence of alignment mismatches especially at the beginning and/or the end of the reads ("soft clipping"), as may be due to primer mispriming. As known to those skilled in the art of bioinformatics, soft clipping information may then be re-aligned in the genomic analysis workflow with specific algorithms in order to further detect structural variants of potential clinical relevance. The genomic data analyzer 120 may thus automatically identify 212 the short reads with soft clipping regions, from the results of the data alignment 232, and configure 233 the data alignment module 121 to operate a further data re-alignment 234 on those reads specifically by taking into account the primer anchors information corresponding to the specific DNA enrichment technology in the alignment algorithm. As will be apparent to those skilled in the art of bioinformatics, a more robust algorithm than Bowtie2 or BWA may be used specifically on those regions, even if less computationally efficient, as only a subset of the whole sequencing data needs to be re-aligned this way.

Depending on the genomic context identifier, the genomic data analyzer 120 may also identify from the alignment data the presence of some regions that are particularly challenging to align, such as homopolymer regions, heteropolymer regions, or other regions with specific repeat patterns. Proper alignment of corresponding next generation sequencing reads is particularly challenging as those multiple repeats cause alignment ambiguities. The genomic data analyzer 120 may thus automatically identify 212 from the results of the raw data alignment 232 a specific genomic context requiring refinement on the reads overlapping those ambiguous regions. The genomic data analyzer 120 may accordingly configure 233 the data alignment module 121 to operate a further data re-alignment 234 on those reads to identify other possible alignment solutions, such as for instance by taking into account the PCR error rate and comparing reads to each other.

The genomic data analyzer 120 may then use the target enrichment technology identifier to configure 241 the variant calling module 122 to execute different variant calling algorithms in accordance with the genomic context (e.g. BRCA1, BRCA2 and TP53 genomic analysis). The variant calling module 122 calls 242 variants on the refined alignment data to produce a first VCF file. In particular, SNPs and short INDELs may be called and annotated by the variant calling module 122 configured to execute a variant calling method to produce a first variant calling information data, comprising a list of variants and their coverage information.

Moreover, in addition to SNPs and short INDELs variant calling or in parallel with SNPs and short INDELs variant calling, intragenic germline CNVs variants (germline CNVs that only affect part of a gene) may be called by the variant calling module 122 to produce a second variant calling data, comprising a list of intragenic germline CNVs of potential clinical relevance. SNPs/INDELs and CNVs variant calling may be executed in parallel or serially by the variant calling module 122. In a possible embodiment, the method of patent application PCT/EP2016/078113 by Sophia Genetics may be used, but other CNV detection algorithms may also be used.

In somatic genomic analysis, the resulting variants may not be accurate enough to be reported by the genomic data analyzer 120. The genomic data analyzer 120 may thus identify 214 a fourth set of characteristics such as the need for variant phasing from the first and or second variant calling results, and configure 243 the variant calling module 122 to refine 244 the variant calling data to be analyzed 245 and reported 250 by the genomic data analyzer 120.

In a possible embodiment, the variant classification module 123 may annotate and prioritize 245 the variant calling data by using information from cancer variant databases such as COSMIC or Clinvar, and/or pathogenicity prediction tools such as Align GVGD, Sift, Polyphen2, Alamut and others, as will be apparent to those skilled in the art of bioinformatics applied to personalized medicine research. In a possible embodiment, the variant classification module 123 may categorize 245 the annotated variant calling data by detecting certain genomic alterations of particular interest, such as for instance biallelic loss of function due to a combination of genomic alterations and chromosomal aberrations in certain tumour suppressor genes.

Finally, the genomic data analyzer 120 may report 250 a set of refined classified genomic variants to an end user, as a result file and/or through a graphical user interface. In a possible embodiment, the genomic data analyzer may report 250 the classified genomic variant information to a further data processor, through a communication network, for instance to an automated tool as a support to medical diagnosis or personalized medicine treatment recommendations. In a possible embodiment, the genomic data analyzer may record 250 the classified genomic variant information into a medical knowledge database, for instance for reference in genomic research or in future clinical trials scientific data.

Alternative—Distributed Automated Next Generation Sequencing Workflow

Other genomic analysis workflows for the genomic data analyzer 120 are also possible. In particular, as will be apparent to those skilled in the art, the proposed variant calling refinement 244 and variant analysis 245 methods may also be configured as a data post-processing stage to refine, analyze, annotate, categorize and/or prioritize genomic variants initially identified from targeted next generation sequencing variant calling 242 performed by a third party genomic analysis workflow. The genomic data analyzer 120 may then acquire the variant calling information from a third party genomic analyzer workflow. In a possible embodiment (not represented), the genomic data analyzer 120 acquires the variant calling information from a third party genomic analyzer workflow as VCF file through a communication network, but other embodiments and file formats are also possible. In a further possible embodiment the genomic data analyzer 120 may also acquire annotated variant information from a third party genomic analyzer workflow. Other embodiments are also possible.

Variant Classification Methods—Exemplary Embodiment

In a preferred embodiment which will now be described in further detail, the variant classification module 123 may be configured to analyze the variant fraction information as may be extracted from the variant calling data, in order to infer unknown variables such as the sample purity (ratio of somatic DNA material in the overall FFPE sample), and to detect the presence of germline heterozygous allelic variants and the presence of different somatic allelic variant fractions due to different chromosomal aberration events, such as those inducing genomic loss-of-heterozygosity (LOH) in the various tumor cells. Indeed, we observed that LOH does not necessarily require a change in copy number. In particular, copy-neutral LOH can occur in situations where the allele harboring a heterozygous mutation is duplicated and the non-mutated allele is deleted. This is a major limitation to state of the art bioinformatics approaches which primarily infer LOH from the coverage signal.

In a possible embodiment, the variant classification module 123 first extracts from the variant calling information data SNPs and their variant fraction, that is the ratio of the number of NGS reads harboring each SNP variant over the total number of reads. The variant classification module 123 further selects as putative germline heterozygous SNPs, for which one may expect a statistical distribution of the variant fraction centered at 50%, across all observed samples as the SNPs which:

are listed in a human reference variant database;
and whose variant fraction is in a range beyond close to 0% and below close to 100%.

In a possible embodiment, the reference database may be dbSNP to identify variants that are commonly found in human genetics, but other embodiments are also possible, for instance Exac or 1000-genomes may be used as alternative reference databases for identifying SNPs commonly found in human genetic variations. In another possible embodiment, clinical variant databases such as Clinvar may be used to exclude SNP variants that are not commonly found in human genetics.

In a possible embodiment, the heterozygous SNP selection range for the variant fraction values may be defined as [0%+Δh0, 100%−Δh100], where the values of Δh0 and Δh100 may be chosen such that Δh0≤5% and Δh100≤5%. In a possible embodiment, the heterozygous SNP selection range may be between 4% and 96%, but other embodiments are also possible, for instance between 5% and 95% or between 3% and 97%.

In practice, we observed that the statistical distribution of the putative germline heterozygous SNPs over all samples may be biased towards a different value than the expected 50% value, such as 47% in some of our experiments. This may be caused by a bias due to the impact of SNPs on capture efficiency when using standard variant fraction estimator algorithms; indeed, we observed that compared to non-mutated fragments, DNA fragments harboring a SNP may have been captured with a lower efficiency, possibly down to 10%.

As will be apparent to those skilled in the art of bioinformatics, the variant classification module 123 may accordingly compensate for capture-bias by estimating the average drop in capture efficiency due to the presence of a SNP in a DNA fragment. In a possible embodiment, the variant classification module 123 may apply an unbiased estimator of the variant fraction, such that:

$$VF = \frac{N_{ALT}}{N_{ALT} + N_{REF}}$$
$$= \frac{\hat{N}_{ALT}}{\hat{N}_{ALT} + \hat{N}_{REF} \cdot e_{ALT}/e_{REF}}$$

where VF is the variant fraction value, $N_{ALT}$ the number of fragments with SNP in the original DNA sample material, $N_{REF}$ the number of fragments without SNP in the original DNA sample material; the number of fragments without SNP in the captured material may be estimated as:

$$\hat{N}_{REF} = N_{REF} \cdot e_{REF}$$

and the number of fragments with SNP in the captured material may be estimated as:

$$\hat{N}_{ALT} = N_{ALT} \cdot e_{ALT}$$

where the loss in capture efficiency due to the presence of a SNP may be defined as:

$$a = e_{ALT}/e_{REF}$$

If the variant fraction estimation was unbiased, then we would expect the variant fraction distribution to have a symmetric mode centered at 50%. The loss a in capture efficiency due to the presence of a SNP may then be experimentally inferred as the value for which the variant fraction distribution across all samples in the pool is maximally symmetric around 50%.

In a possible embodiment, the variant classification module 123 may estimate the loss a in capture efficiency to unbias the variant fraction for each putative germline heterozygous SNP i from:
- the number of reads $N_{alt,i}$ supporting the SNP i;
- the number of reads $N_{ref,i}$ supporting the reference genome;

by first calculating the unbiased variant fraction $x_i$ of a SNP i, according to the following formula:

$$x_i = \frac{N_{alt,i}}{N_{alt,i} + aN_{ref,i}}$$

where a is the ratio between the capture efficiency of reads including a SNP and the capture efficiency of reads matching the reference. The parameter a is unknown and has to be inferred from data. As will be apparent to those skilled in the art of statistics, various methods may be employed to this end. In a possible embodiment, for any possible value of a (e.g., 0.5<a<1), the variant classification module 123 may compute the unbiased variant fractions $\{x_1, x_2, \ldots, x_N\}$ of putative heterozygous SNPs and may then estimate distribution of variant fractions p(x) by using, e.g., a kernel density estimation technique:

$$p(x) = \frac{1}{N} \sum_{i=1}^{N} K(x - x_i)$$

where K(x) is an even function. In a possible embodiment, a Gaussian function with standard deviation 1% may be used, but other embodiments are also possible. The degree of symmetry around 50% of p(x) may then be calculated by various algorithms. For instance, in a possible embodiment the following RMSE-based score may be calculated by the variant classification module 123:

$$E(a) = \int_0^{+C} [p(50+x) - p(50-x)]^2 dx$$

where C is a parameter of choice that can be fixed e.g. to 5% in an automated variant classification module 123, as will be apparent to those skilled in the art of bioinformatics. Note that since $x_i$ (used to compute p(x)) depends on a, the RMSE-based score also depends on a. The optimal parameter a may then be obtained by finding the value under which E(a) is minimized. The variant classification module 123 may solve this problem by using standard optimization techniques, such as a line-search algorithm. The above embodiment has been presented by way of example and not limitation. Other embodiments are also possible; as will be apparent to those skilled in the art of statistics, the variant classification module 123 may be adapted to implement various methods and/or parametrizations to unbias the variant fraction distribution.

Figure 3:
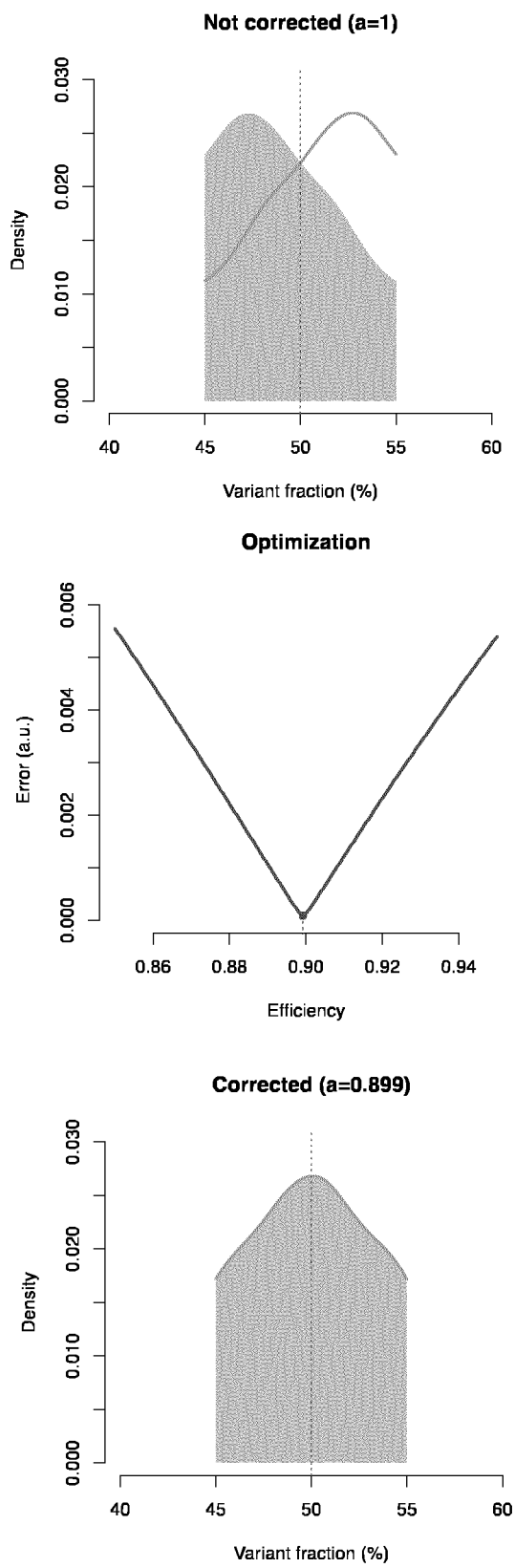
FIG. 3 illustrates the unbiasing of the putative heterozygous germline SNPs variant fraction distributions over all samples towards a peak at 50%.

FIG. 3 illustrates the uncorrected and the corrected variant fraction distributions in an experiment where the value of a is measured at 0.9, corresponding to a loss in capture efficiency of 10%. In our experiments, we also observed that the resulting unbiased variant fraction distribution of putative germline heterozygous SNPs across all samples is characterized by both a high variability and a high degree of symmetry around the 50% axis.

First hypothesis: The high level of variability may be due to a low amount of DNA material due to high levels of FFPE degradation, but also to the presence of cancer-specific CNVs.

Figure 4:
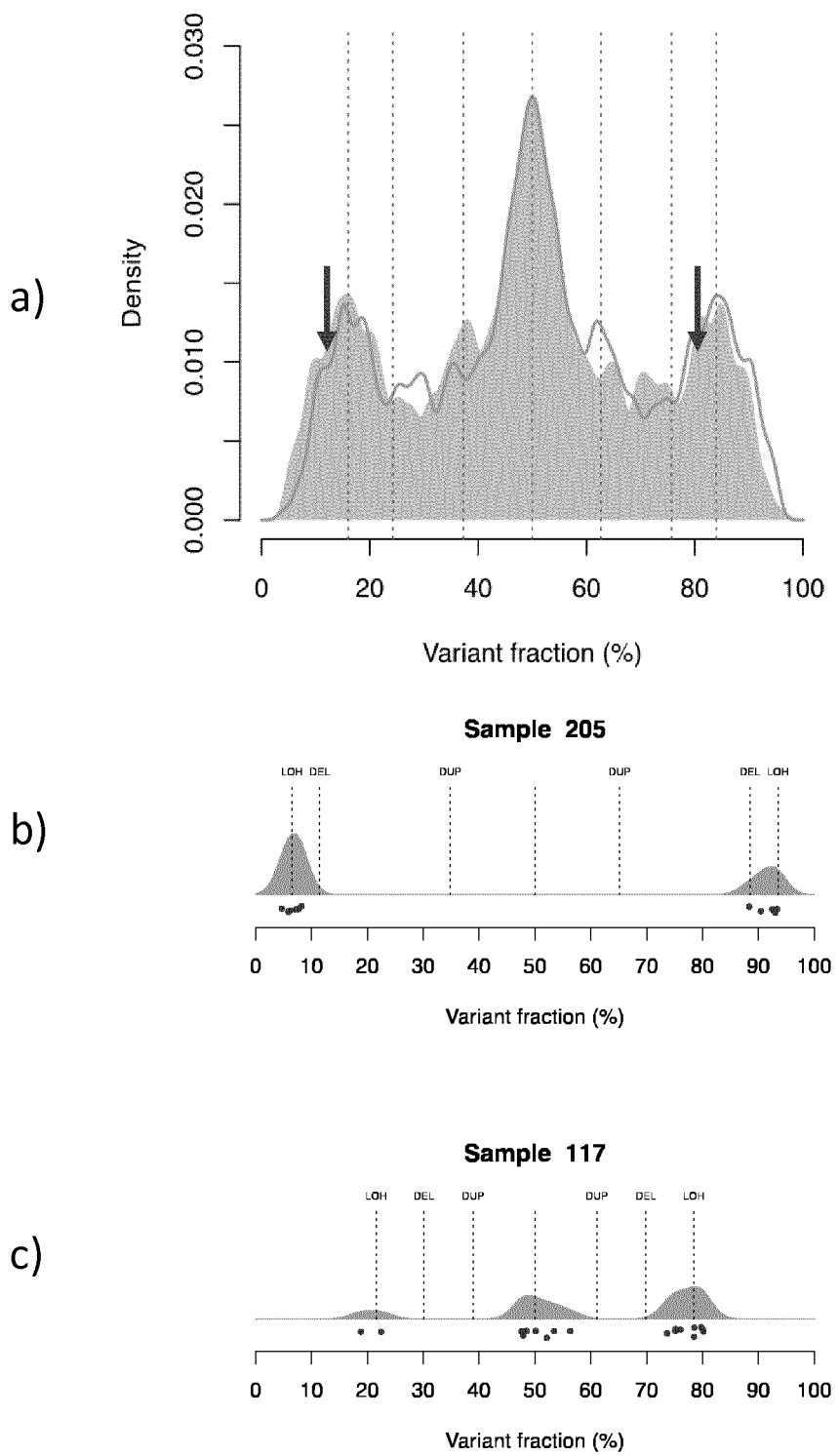
FIG. 4 illustrates the symmetry of the putative heterozygous germline SNPs variant fraction distributions secondary peaks over all samples a) as well as in different patients b) and c).

Second hypothesis: The high level of symmetry may be observed with secondary peaks, as illustrated on FIG. 4*a*), one at around 50-ΔVF % (e.g., 15%, for ΔVF=35%) and one at around 50+ΔVF % (e.g., 85%, for ΔVF=35%). Interestingly, a high degree of symmetry is also observed within individual samples, as illustrated on FIG. 4*b*) and FIG. 4*c*) respectively. This may be due to a large number LOH events of germline heterozygous SNPs in the somatic cells, due to a second-hit alteration in the tumor cells, in accordance with the Knudson's two-hit theory of tumorigenesis.

Figure 5:
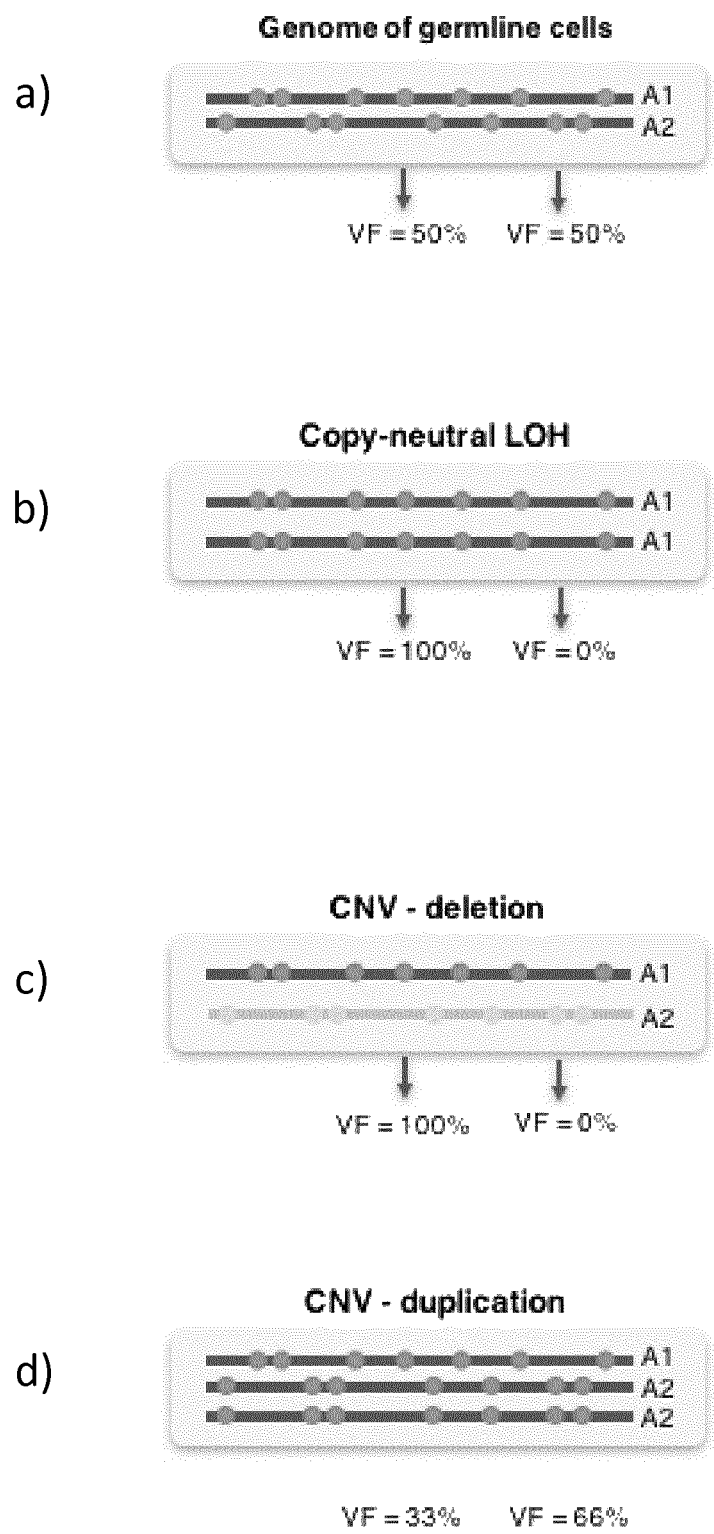
FIG. 5 schematically represents the impact on heterozygous germline SNPs of different chromosomal aberration events causing loss-of heterozygosity (LOH).

It is therefore of interest to map the experimental data against a statistical model jointly taking into account the above two hypotheses. With regards to the second hypothesis, FIG. 5 illustrates that different LOH-inducing chromosomal aberrations may result into specific variant fraction distributions peaks:

FIG. 5*a*) shows a schematic representation of the genomic region of a germline cell, wherein A1 and A2 denote two different alleles. Each circle dot represents a germline heterozygous SNP. The variant fraction distribution of any of these SNPs may thus be modelled as a single peak at 50% ("no-LOH").

FIG. 5*b*) shows a schematic representation of the same genomic region of a cancer cell affected by copy-neutral loss of heterozygosity ("CN-LOH"), wherein allele A2 was deleted and allele A1 was duplicated via, e.g., homologous recombination repair. Each circle dot represents a germline-derived SNP. As a result of this copy-neutral LOH chromosomal aberration:

Germline heterozygous SNPs harbored in allele A1 became homozygous. The variant fraction distribution of any of these SNPs may be modelled as a single peak at 100%, while the copy number remains 2 as in germline cells.

Germline heterozygous SNPs harbored in allele A2 were lost. The variant fraction distribution of any of these SNPs may be modelled as a single peak at 0%, while the copy number remains 2 as in germline cells.

FIG. 5*c*) shows a schematic representation of the same genomic region of a cancer cell affected by a somatic deletion ("LOH-DEL") of allele A2:

Germline-derived SNPs harbored in allele A1 (dark circle dots) became hemizygous. The variant fraction distribution of any of these SNPs may be modelled as a single peak at 100%, while the copy number is 1.

Germline-derived SNPs harbored in allele A2 (clear circle dots) were lost. The variant fraction distribution of any of these SNPs may be modelled as a single peak at 0%, while the copy number is 1.

FIG. 5*d*) shows a schematic representation of the same genomic region of a cancer cell in which allele A2 was duplicated ("LOH-DUP"):

Germline-derived SNPs harbored in allele A1 are present in only one allele out of three. The variant fraction distribution of any of these SNPs may be modelled as a single peak at 33%, while the copy number is 3.

Germline-derived SNPs harbored from allele A2 are present in two alleles out of three. The variant fraction distribution of any of these SNPs may be modelled as a single peak at 66%, while the copy number is 3.

Figure 6:
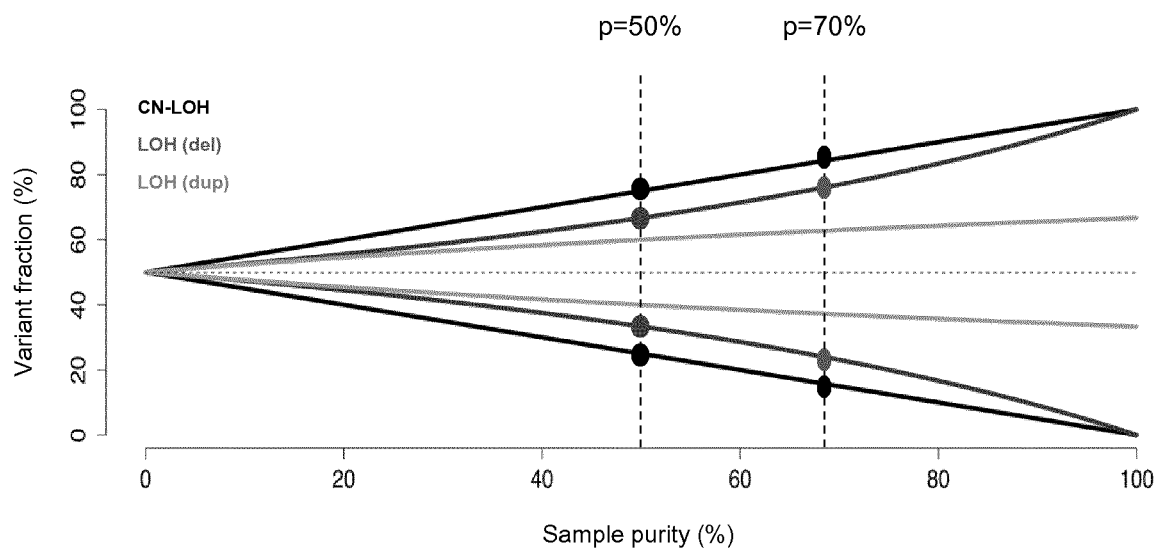
FIG. 6 shows that different chromosomal aberrations causing loss-of heterozygosity (LOH) yield different variant fraction symmetrical values around the 50% for a significant range of purity values.

With regards to the first hypothesis, FIG. 6 illustrates how the variant fraction distributions of a germline heterozygous SNP respectively affected by a copy-neutral LOH (black—CN-LOH), a deletion-induced LOH (dark grey—LOH-DEL) and a duplication-induced LOH (clear grey—LOH-DUP) may vary with sample purity. In particular, as pointed out for example purities of p=50% or p=70% respectively, the above listed different LOH-inducing mechanisms result in clearly different variant fraction distribution symmetrical values relative to the 50% variant fraction axis. In this situation, we observed that the observed variant fraction distributions can be used to reliably jointly infer sample purity and detect separate as well as combined genomic alteration events, as will now be described in further detail.

Thus, for each possible purity ratio of a patient sample, the variant classification module 123 may estimate the value of the theoretically symmetrical variant fraction distribution of somatic chromosomal aberration events. For instance, "NO-LOH", "CN-LOH", "LOH-DUP" and "LOH-DEL" events as described above all result in a different theoretical variant fraction value, but other events could be assessed similarly in more complex applications (e.g. frequently found subclonal alteration events in other cancers).

Figure 7:
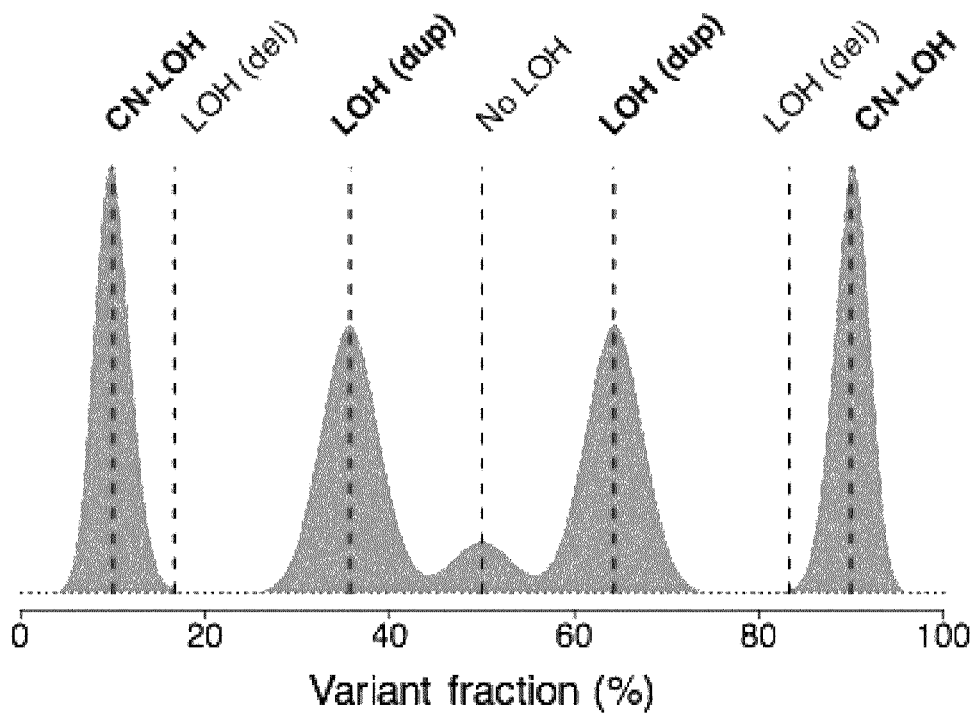
FIG. 7 shows different theoretical variant fraction distributions for two exemplary genomic alteration scenarios a) and b), both calculated for a purity ratio at 80%.
Figure 7:
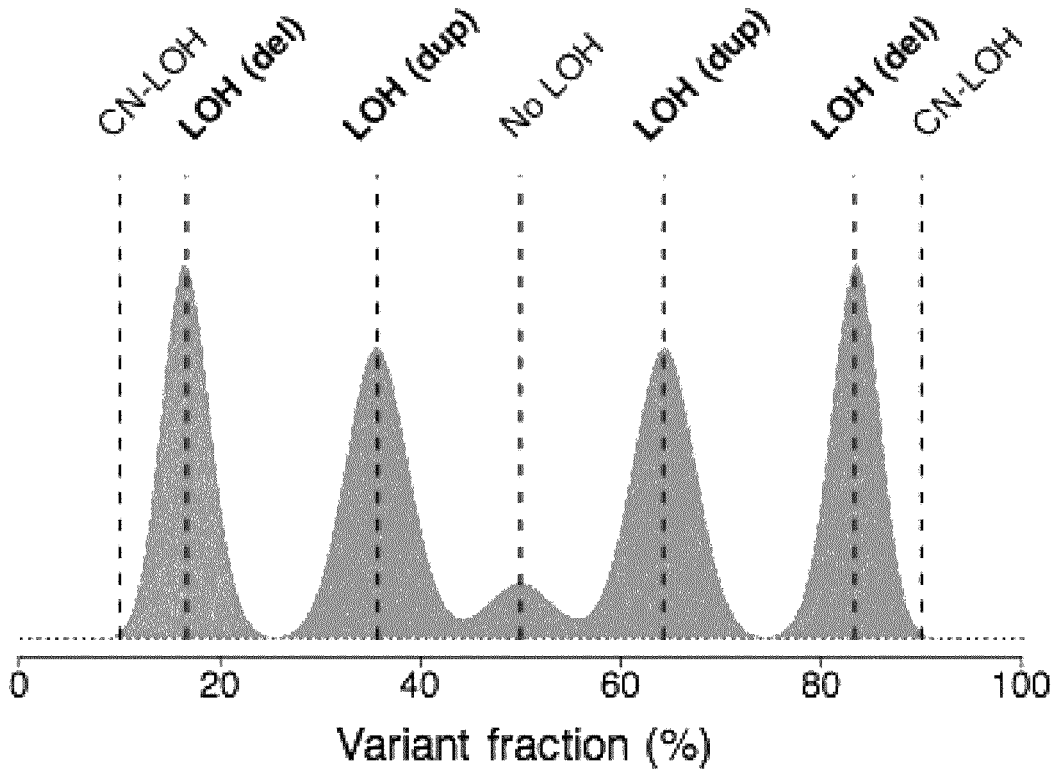

The variant classification module 123 may thus compare the observed variant fractions of the putative germline heterozygous SNPs corresponding to this with the theoretically symmetrical variant fraction values for different purity ratios. FIG. 7a) and FIG. 7b) respectively illustrate how two exemplary patient sets of putative germline heterozygous SNPs map to those values, as represented by dashed lines for a purity ratio of p=80%:

FIG. 7a): purity p=80%—in this patient, the observed symmetrical peaks of the variant fraction distribution for putative germline heterozygous SNPs can be mapped to the CN-LOH and to the LOH-DUP theoretical values, which indicates that part of the genome is affected by copy-number LOH (CN-LOH) while part of the genome affected by a somatic duplication (LOH dup);

FIG. 7b): purity p=80%—in this patient, the observed symmetrical peaks of the variant fraction distribution for putative germline heterozygous SNPs can be mapped to the LOH-DEL and to the LOH-DUP theoretical values, which indicates that part of the genome affected by a somatic deletion (LOH del) while part of the genome is affected by a somatic duplication (LOH dup).

Thus, for each chromosomal aberration inducing a theoretically symmetrical variant fraction distribution and for each possible purity ratio, the variant classification module 123 may estimate the theoretical variant fraction value for the putative germline heterozygous SNPs corresponding to this scenario for this purity ratio, and evaluate how closely the unbiased observed variant fraction distribution fits to the theoretical variant fraction distribution value corresponding to this scenario. As will be apparent to those skilled in the art of bioinformatics, this fit may be evaluated by different statistical methods. In a simple embodiment, the variant classification module 123 may calculate a distance from the unbiased observed variant fraction distribution to the theoretical variant fraction distribution value corresponding to this scenario. The variant classification module 123 may then calculate an overall distance and select the purity ratio for which the computed statistical distance is minimal over all scenarios.

As will be apparent to those skilled in the art of statistical analysis, various statistical algorithms may be used to this end. In a preferred embodiment, the variant classification module 123 may fit a mixture model to the observed variant fraction distribution of the overall putative germline heterozygous SNPs in the variant calling data for each possible value p of the sample purity, the modeled variant fraction distribution values being calculated as a function of the sample purity p. The mixture model may then be fitted to the data by minimizing a cost function measured between the observed and the theoretical variant fraction expected for the most likely chromosomal aberration scenario.

For instance, a simple embodiment will now be described in further detail:

Step 1: Infer Purity p

For each possible purity p between 0% and 100% the variant classification module 123 may compute a cost function model-prediction error E(p) as the root mean squared error (RMSE) of the SNP variant fraction distribution computed with respect to its closest theoretical variant fraction values according to the following equation:

$$E(p) = \sqrt{\frac{1}{N}\sum_{i=1}^{N}\left[\min_{d \in D(p)}(x_i - d)\right]^2}$$

where $x_i$ is the unbiased variant fraction of the putative heterozygous SNPs i in the set of N putative heterozygous SNPs identified by the variant classification module 123, and D(p) is the set of theoretically symmetric variant fractions predicted by the variant classification module 123 for each possible scenario under the assumption of purity=p. Indeed, the position of these theoretical variant fractions depends on the purity p, as illustrated for instance in the FIG. 6 example, so the model-prediction error also depends on the purity variable p.

As will be apparent to those skilled in the art of statistics, the variant classification module 123 may then apply an optimization algorithm to infer from the experimental data the optimal purity $p_{optimal}$ for which E(p) is minimized. In a possible embodiment the variant classification module 123 may be adapted to apply a line-search algorithm to determine the optimal purity $p_{optimal}$:

$$p_{optimal} = \underset{p}{\mathrm{argmin}}\{E(p)\}$$

We note that other embodiments are also possible. For instance, the variant classification module 123 may fit a mixture model with theoretical value components corresponding to the different scenarios, using either the Expectation-Maximization (EM) algorithm or a Markov-Chain Monte-Carlo (sampling) approach, as will be apparent to those skilled in the art of bioinformatics. In a preferred embodiment, the mixture model may be a Gaussian Mixture Model (GMM) but other embodiments are also possible, depending on the specifics of the genomic variant distributions.

Step 2: Detect Chromosomal Aberrations on a Gene-by-Gene Basis

Once the purity has been inferred over the putative heterozygous SNPs throughout all genes in the sample, the variant classification module 123 may refine the analysis by detecting the most likely chromosomal aberrations for each gene separately, in order to facilitate the further identification and classification of loss-of-function genomic alterations of interest to report to the end user. In the exemplary application of biallelic loss-of-function genomic alterations detection, the possible chromosomal aberrations of interest at this stage may match the following hypotheses (FIG. 5):

$H_1$: No LOH
$H_2$: LOH-dup
$H_3$: LOH-del
$H_4$: CN-LOH

In a possible embodiment, for each gene to analyze, for instance respectively BRCA1, BRCA2 and TP53 in the case of ovarian cancer, the variant classification module 123 may apply the following method:

For each possible event $H_i = \{H_1, H_2, H_3, H_4\}$, a model-prediction error may be computed as the root mean squared error (RMSE) of the gene SNP variant fraction distribution computed with respect to its closest theoretical variant fraction values according to the following equation:

$$E(p_{optimal}, H_i) = \sqrt{\frac{1}{M} \sum_{i=1}^{M} \left[ \min_{d \in D(p_{optimal}, H_i)} (x_i - d) \right]^2}$$

where $x_i$ is the unbiased variant fraction of the putative heterozygous SNPs I in the set of M putative heterozygous SNPs identified by the variant classification module 123 in the gene to analyze and $D(p_{optimal}, H_i)$ is the subset of theoretical variant fraction values predicted for the alteration event hypothesis $H_i$ in the gene to analyze under the assumption of purity=$p_{optimal}$ In the example of FIG. 5, there is one value for $H_1$ and two symmetrical values for the other hypotheses.

As will be apparent to those skilled in the art of bioinformatics, the variant classification module 123 may also apply other methods than the RMSE to identify the most likely alteration event hypothesis. For instance, when a mixture model has been used in step 1, Mixture Model Classifiers as known in the art may be applied by the variant classification module 123 to identify the most likely alteration event hypothesis.

Further Embodiment—Automated Identification of Intragenic Germline CNVs from Heterogeneous Somatic Samples In a possible further embodiment, the information about the gene LOH status and sample purity may also further facilitate the identification of intragenic germline CNVs. The coverage signal of each patient sample in the multiplexed sequencing pool of samples may be normalized and a list of intragenic CNVs may be detected using for instance the method of patent application PCT/EP2016/078113. Due to the intrinsic heterogeneity of the cancer cell sub-clonal variants, the presence of a mix of germline and somatic cells in the tumor samples and the FFPE targeted sequencing coverage of generally low quality, the coverage signal is particularly noisy and it is difficult to directly detect the CNV variants without further knowledge on the underlying sample. In order to establish the relevance of each intragenic germline CNVs, the coverage signal may be further analyzed taking into account the information about the gene LOH status and sample purity p as formerly derived from the putative germline heterozygous SNP variant faction analysis.

While the above examples have been described for simple somatic event models of copy number values between 1 and 3, it will be apparent to those skilled in the art of bioinformatics that more complex scenarios may also be modelled in a similar way, for instance with copy number values larger than 3, in particular in cases where more genes are covered by the experimental panel.

Identification of Biallelic Loss-of-Function Alterations

The variant classification module 123 may then combine detected information on likely pathogenic SNPs, INDELs, intragenic germline CNVs and LOH status to classify and report them to facilitate their interpretation. As will be apparent to those skilled in the art of oncogenomics, in the case of tumor suppressor genes, the primary information of interest to the end user is whether the gene has lost its function. This loss of function may be due to a combination of at least two genomic alterations. Somatic variant databases such as Clinvar record known SNP and INDEL variants of likely pathogenicity. Some of those variants, regardless of their germline or somatic origin, may be combined with chromosomal aberrations in tumor cells, causing the biallelic loss of function of the gene. In the exemplary application of ovarian cancers targeted treatment with oliparib, as recently published by Douherty et al. in "*Biological and clinical evidence for somatic mutations in BRCA1 and BRCA2 as predictive markers for olaparib response in high-grade serous ovarian cancers in the maintenance setting*", Oncotarget Advance Publications 2017, published online May 4, 2017, the secondary information of interest is whether the detected gene loss of function is due to:

(1) biallelic pathogenic variants in BRCA1 or BRCA2 (for which homologous recombination repair is likely defective and may be targeted by dedicated medication, such as for instance PARP inhibitors)

or (2) potentially biallelic variants in BRCA1 or BRCA2 (for which the genomic analysis method cannot confirm the exact status, thus possibly requiring supplemental analysis)

or (3) monoallelic variants in BRCA1 or BRCA2.

In a possible embodiment, the variant classification module 123 may annotate and prioritize 245 the variant calling data of each patient tumor sample by using information from cancer variant databases such as COSMIC or Clinvar, and/or pathogenicity prediction tools such as Align GVGD, Sift, Polyphen2, Alamut and others to identify SNPs and INDELs of likely pathogenicity, as will be apparent to those skilled in the art of bioinformatics applied to personalized medicine. The variant classification module 123 may further determine how these mutations have been combined in the cancer cells with the chromosomal arrangements as previously inferred to determine, for each gene to be analyzed, a combination of genomic alterations possibly causing a biallelic loss of function of the gene.

Figure 8:
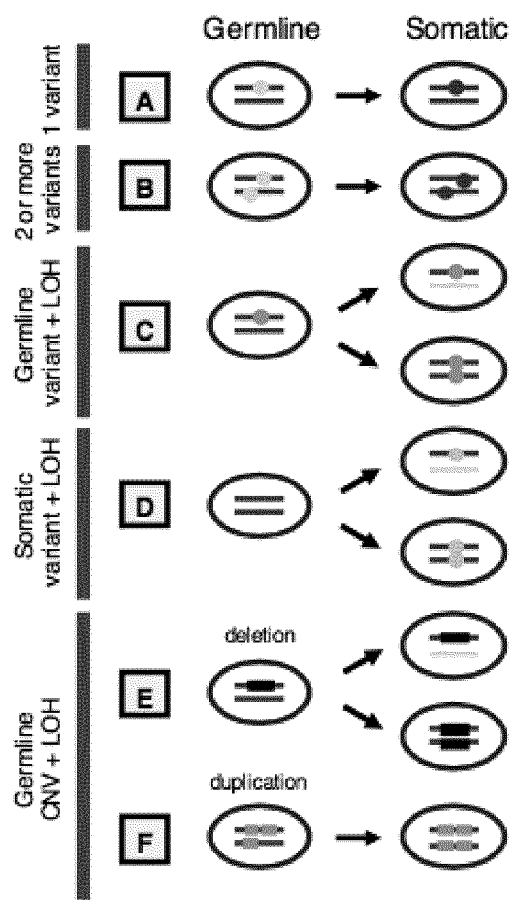
FIGS. 8a and 8b schematically represent six different categories of genomic alterations as may be detected by an exemplary embodiment of the variant classification method.

In the exemplary application of ovarian cancer analysis, for each gene in each sample, the analyzed genes may be classified in six different categories, based on their resulting genomic aberrations, as represented in FIG. 8a):

Class A: Genes affected by a single SNP or INDEL of likely pathogenicity.

Class B: Genes affected by at least two SNPs or INDELs of likely pathogenicity.

Class C: Genes affected by a likely pathogenic, germline-derived variant with positive LOH status. This class may comprise cases in which a heterozygous germline SNP or INDEL became hemizygous because of a somatic deletion of the non-mutated allele or homozygous because of a concomitant duplication of the mutated allele (i.e., copy-neutral LOH).

Class D: Genes affected by a likely pathogenic, somatically acquired variant with positive LOH status. As for class C, this may comprise cases of copy-neutral LOH and cases in which LOH was induced by a somatic deletion of the non-mutated allele.

Class E: Genes in which an intragenic heterozygous single- or multi-exon deletion (CNV=1) of germline origin was combined with copy-neutral LOH or full-gene somatic deletion of the non-mutated allele.

Class F: Genes in which a single- or multi-exon intragenic duplication (CNV=3) of germline origin was combined with full-gene deletion of the non-mutated allele.

In some samples, the detected information on likely pathogenic SNPs, INDELs, intragenic germline CNVs and LOH status may not be sufficient for the variant classification module 123 to classify and report the gene into a specific category. For instance, the variant classification module 123 may identify positive LOH status without confirming whether the likely pathogenic variant is of germline (class C) or somatic (class D) origin. The variant classification module 123 may accordingly categorize those variants as C/D (class C or class D).

In a possible embodiment, the above classes may be used by the variant classification module 123 to also determine the loss-of-function allelic type:

All of the genes affected by a genomic aberration of class C-F and in which the LOH status could be determined with good confidence level may be classified as affected by biallelic pathogenic variants (1).

All of the genes carrying a genomic aberration of class B (i.e., two or more likely pathogenic variants) may be classified as affected by potential biallelic pathogenic variants (2). The reason for this is that NGS short-reads data makes it particularly challenging to phase variants which are far apart. Thus, it is often not possible without additional analysis to exclude that these variants occurred on the same allele. All of the genes affected by a genomic aberration of class C-F and in which the LOH status could not be determined with good confidence level may also be considered as affected by potential biallelic pathogenic variants. In this case, potentially reflects a lower level of confidence, compared to likely.

All of the genes affected by a genomic aberration of class A may be classified as carrying a monoallelic pathogenic variant.

In a possible embodiment, no distinction in made between germline-derived, somatically acquired and subclonal variants, but other embodiments are also possible, for instance by discriminating them into sub-classes A1, A2, A3 . . . and B1, B2, B3 . . . , subject to the theoretical variant fraction distribution scenarios used in the initial variant classification analysis steps.

The variant classification module 123 may then report 250 the detected genomic variant classes to the end user in various formats. In a possible embodiment, a list may be used to report for each gene the actual detection status (1) biallelic (2) potentially biallelic (3) monoallelic or (4) undetermined, and the class A, B, C, D, E, F or undetermined. In a possible embodiment illustrated on FIG. 8b), a table may be used to report for each gene (here BRCA1, BRCA2 and TP53) and for each sample in the pool with a color code the actual detection status as well as the detected class, marked into the table cell—for instance in FIG. 8b) dark cells represent monoallelic status, clear cells represent potentially bi-allelic status, marked medium grey cells marked represent bi-allelic status, and unmarked medium grey cells represent undetermined status. Grey crosses further mark samples in which homologous recombination repair is likely defective and sensitive to oliparib as a result of BRCA1/BRCA2 biallelic variants, as detected by the proposed methods.

Automated Genomic Data Analyzer Workflow

Figure 9:
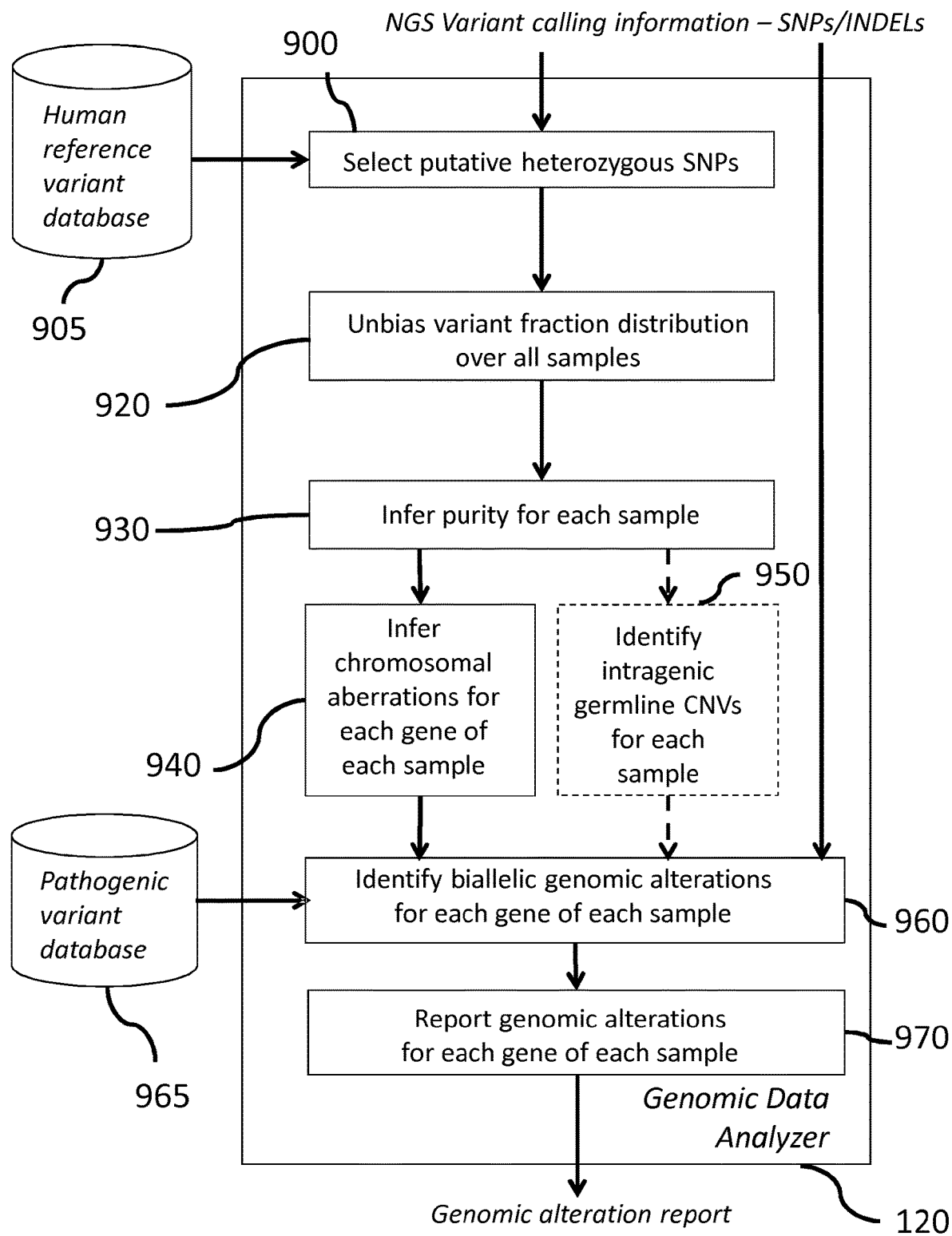
FIG. 9 shows a flowchart of a possible embodiment of the proposed variant classification method.

FIG. 9 illustrates a possible automated workflow of a genomic data analyzer 120 adapted to analyze 245 with a variant classification module 123 the next generation sequencing variant calling information from somatic patient samples to report likely pathogenic biallelic genomic alterations of analyzed genes in a genomic alteration report, comprising:

Selecting 900 a set of putative heterozygous SNPs from the variant calling data in accordance with a human reference database of SNP variants;

Unbiasing 920 the variant fraction distribution of the putative heterozygous SNPs over all samples;

Inferring 930 the purity for each sample;

Inferring 940 chromosomal aberrations for each analyzed gene of each sample;

Identifying 960, for each analyzed gene of each sample, genomic alterations possibly causing the biallelic loss of function of the gene as the combination of inferred chromosomal aberrations and SNPs or INDELs of likely pathogenicity in accordance with a pathogenic variant database 965;

Reporting 970 detected genomic alterations for each analyzed gene of each sample.

In a further embodiment, the genomic data analyzer may also be adapted to identify 950 intragenic germline CNVs for each sample and also take them into account in identifying 960 biallelic genomic alterations for each gene of each sample.

Advantages of the Proposed Method Over Prior Art Methods

The genomic data analyzer 120 does not need germline reference samples to operate the variant classification analysis and instead can operate solely on variant calling information from samples comprising a mix of germline and somatic cells of unknown purity, such as FFPE tumour samples. This is a significant advantage over prior art published methods which separately analyze germline and somatic variants, both in terms of routine diagnosis costs and in terms of genetic counselling as may be required for germline analysis due to the possible relationship of germline mutations with other pathologies in the patient and/or its siblings.

As will be apparent to those skilled in the art, another limitation of prior art methods is that the genomic data signals out from sequencing such samples are of low quality and particularly challenging to analyze without proper data pre-processing. In particular, as we experimented with prior art bioinformatics analysis methods applied to somatic FFPE tumour samples sequencing data without germline sample references, the coverage signal alone was not sufficient for the genomic data analyser 120 to reliably infer the presence of somatic CNVs that affected entire genes. The reasons for this are: i) the frequent presence of somatic CNVs in ovarian cancer patients; ii) the fact that, in some samples, the coverage signal was affected by an important presence of noise, which was likely induced by formalin-fixed paraffin-embedding; iii) the fact that somatic samples do not simply comprise a homogeneous population of cancer cells, but also include an unknown fraction of germline cells. Together with the absence of reference samples, these factors prevented us from performing an appropriate coverage normalization. In contrast, the proposed methods grounded on statistical modelling and proper processing, with a variant classification data processor module, of the variant fraction distribution data enables to overcome these limitations and to detect chromosomal aberration events such as LOH induced by somatic deletions or duplications. Importantly, since our approach fully relies on processing the variant fraction information rather than the coverage signals, copy-neutral LOH events can also be detected.

The genomic variant classification report may further facilitate personalized diagnosis and treatment of pathologies such as cancers by identifying whether the sample alterations are biallelic solely from next generation sequencing variant calling information without requiring complementary assays, even with low coverage signals and without the need for dedicated variant phasing bioinformatics methods in the genomic data analyzer 120 workflow, thus enabling lower cost genomic analysis than prior art methods and assays.

While the proposed methods have been described as a standalone workflow, it will be apparent to those skilled in the art of bioinformatics that for certain applications they may also be combined or complemented with other methods, in parallel with the proposed workflow or as additional steps, in order to further improve the specificity and sensitivity of the overall genomic analysis results. For instance, the proposed method may complement the method of patent application PCT/EP2016/078113 by Sophia Genetics to better detect germline CNVs from somatic samples, but other embodiments are also possible.

Experimental Results

Figure 10:
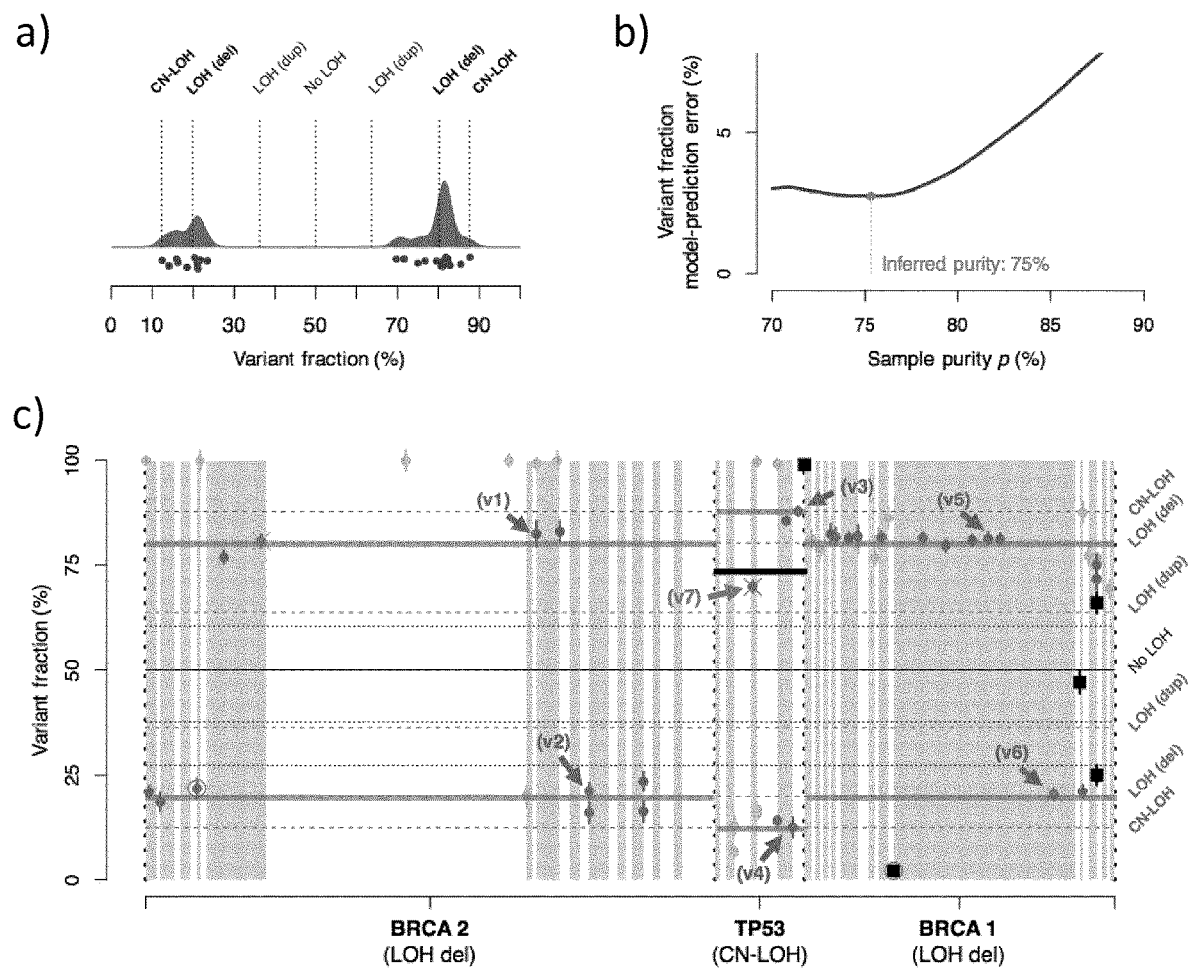
FIG. 10 shows the results obtained with the proposed variant detection method out of variant calling information resulting from the genomic analysis of an FFPE ovarian cancer patient sample with targeted next generation sequencing on the BRCA1, BRCA2 and TP53 genes.

FIG. 10 shows the results obtained with the proposed variant detection method out of variant calling information resulting from the genomic analysis of an FFPE ovarian cancer patient sample with targeted next generation sequencing on the BRCA1, BRCA2 and TP53 genes. Putative germline heterozygous SNPs were first identified from the variant calling information and their variant fraction distribution was unbiased, as shown in FIG. 10a) where the black dots represent the individual putative germline heterozygous SNPs and the grey area their variant fraction distribution. Vertical dashed lines show the theoretical variant fraction values predicted for germline-derived SNPs affected by four different alteration event hypotheses, namely: no loss of heterozygosity ("NO-LOH"), copy-neutral LOH ("CN-LOH"), deletion-induced LOH ("LOH-DEL") and duplication-induced LOH ("LOH-DUP").

The unbiased variant fraction distribution of FIG. 10a) exhibits variant fraction peaks which can be mapped to a scenario of a sample purity of 75% as the value minimizing the prediction-error of a statistical model of the variant fraction distribution, as illustrated in FIG. 10b). This corresponds to a somatic alteration scenario characterized by the presence of LOH in all genes BRCA1, BRCA2 and TP53 as illustrated in FIG. 10c). While in BRCA1 and BRCA2 LOH was induced by a somatic deletion (multiple SNPs mapped around the symmetrical 20% and 80% variant fraction peaks corresponding to the "LOH-DEL" theoretical variant fraction model for a purity of 75%), we found that TP53 underwent copy-neutral LOH (multiple SNPs mapped around the symmetrical 12% and 88% variant fraction peaks corresponding to the "CN-LOH" theoretical variant fraction model for a purity of 75%).

Exemplary Application to Precision Medicine Cancer Diagnosis and Treatment Selection This information may be further used for detecting the most relevant variants of likely pathogenicity in the cancer cells as follows. First, most of the variant fractions observed in this particular sample correspond to theoretical scenario predictions made for germline-derived variants (FIG. 10c) solid gray lines). These variants may thus be classified as germline-derived. Furthermore, a positive LOH status may be attributed to germline-derived variants whose variant fraction is larger than 50% (FIG. 10c) variants v1, v3 and v5). In contrast, germline-derived variants with variant fraction smaller than 50% (FIG. 10c) variants v2, v4 and v6) correspond to lost variants, carried by the allele that was somatically deleted. Since these variants are no longer present in the somatic cells, their LOH status may be classified as negative. Interestingly, the variant fraction of a likely pathogenic TP53 SNP2 (FIG. 10c), v7) does not match any of the theoretical predictions made for germline-derived variants, but rather corresponds with the theoretical value expected in cases where a somatically acquired SNP was subsequently affected by copy-neutral LOH (FIG. 10c) black line). Overall, this analysis allows us to infer that cancer cells from this sample are likely affected by a biallelic TP53 variant.

Variant fraction analysis for the same scenario models as illustrated in FIG. 10 was performed on a pool of sixty individual samples, resulting in the identification and classification of 100 variants most likely pathogenic. The number of likely pathogenic variants identified in each individual sample varied between 0 and 4. The majority of these variants were found to be missense SNPs and frameshift INDELs. Variant origin and LOH status could be determined respectively in 70% and 52% of likely pathogenic variants. Our results revealed the presence of 18 germline-derived variants affected by LOH, 20 somatic variants affected by LOH as well as 5 somatic subclonal variants of likely pathogenicity. Amongst the 30 variants whose origin could not be identified, 9 had positive LOH status. We found that TP53 carried at least one likely pathogenic in about 90% of the samples, while 8% of the samples carried a likely pathogenic BRCA2 mutation of germline origin. Finally, among the sixty samples that were analyzed, 14 carried a germline-derived, likely pathogenic BRCA1 variant.

Figure 11:
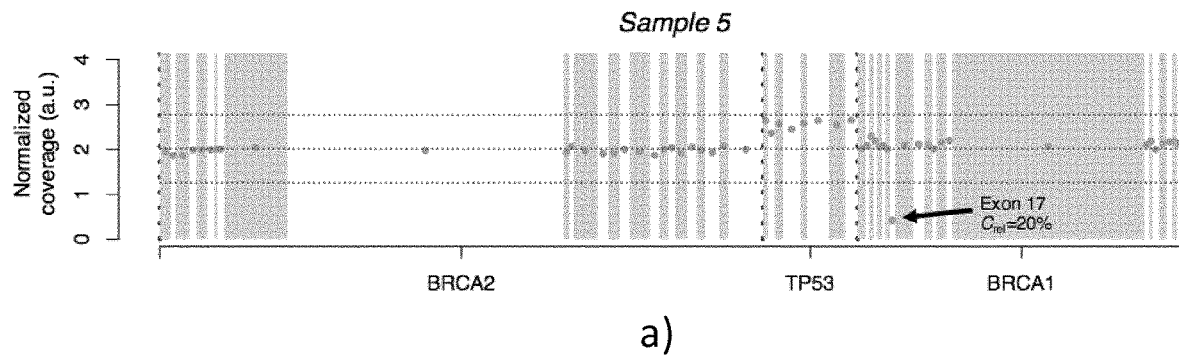
FIG. 11 illustrates an example of how an embodiment of the proposed variant classification method may help further detection of germline intragenic CNV mutations.
Figure 11:
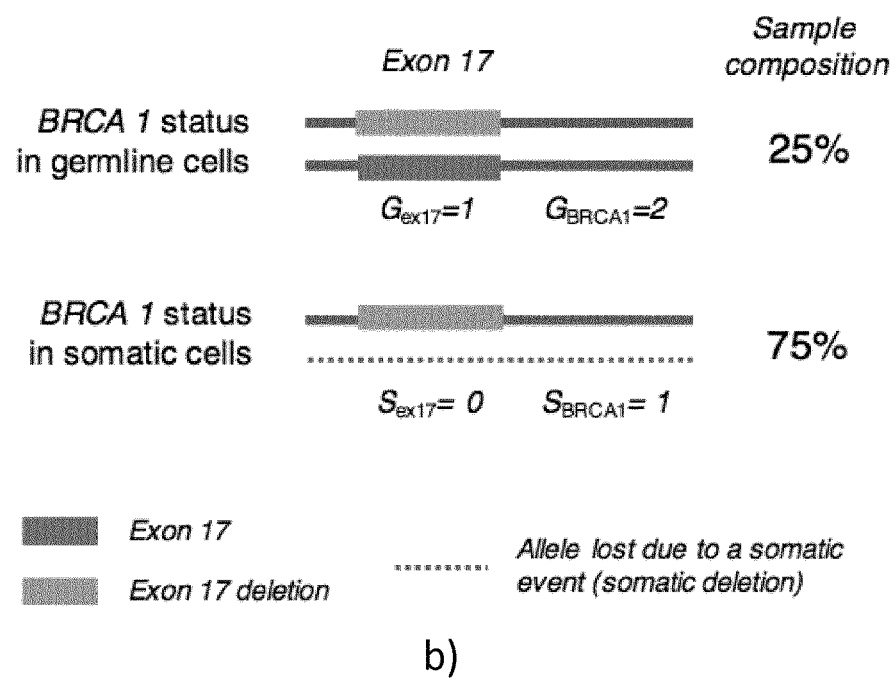

A further analysis also enabled to identify germline CNVs on the same patient as illustrated on FIG. 10). FIG. 11a) shows an example of a normalized coverage signal for BRCA2, TP53 and BRCA1 for the variant calling information for this patient sample. Each dot shows the average normalized coverage observed in a single exon. Gray and white areas correspond to different exons. The normalized coverage has arbitrary units (a.u.) and cannot be directly interpreted as the total number of alleles (i.e., copy number), but it still enables to infer relevant information: the exon17 genomic region of gene BRCA1 shows a significant coverage drop. The normalized coverage ratio between exon 17 and the other exons in BRCA1 is measured as Cre1=20.0%. Under the assumption that this sample comprises a mix of a homogenous population of cancer cells and a homogeneous population of germline cells, the relative coverage observed in exon 17 is given by:

$$C_{rel} = \frac{p \cdot S_{ex17} + (1-p) \cdot G_{ex17}}{p \cdot S_{BRCA1} + (1-p) \cdot G_{BRCA1}}$$

where $S_{ex17}$ and $G_{ex17}$ are the number of copies of exon 17 present in somatic and germline cells respectively, $S_{BRCA1}$ and $G_{BRCA1}$ are the number of copies of the other BRCA1 exons present in somatic and germline cells, respectively, and p denotes the sample purity. The sample purity may be inferred as the value minimizing the prediction error of the mathematical model accounting for the variant fraction of putative heterozygous germline SNPs found in BRCA1, BRCA2 and TP53, in this experiment p=75% as shown in FIG. 10b).

The BRCA1 status of this sample 5 is represented schematically in FIG. 11b). In germline cells (top), BRCA1 was present in two copies (GBRCA1=2), except for exon 17, which had only one copy (Gex17=1, dark grey) as a result of a heterozygous germline deletion (soft grey). In somatic cells (bottom), BRCA1 was only present in one allele (SBRCA1=1), as a result of a somatic full-gene deletion of the non-mutated allele (black dotted line), as formerly inferred from the putative germline heterozygous SNP analysis. Moreover, the only allele left in cancer cells carried an exon 17 deletion (Sex17=0). Biologically, this means that BRCA1 was affected by a germline heterozygous deletion of exon 17 as well as by a somatic deletion of the non-mutated allele. Overall, these results indicate that in this patient cancer cells, both alleles list the BRCA1 tumor suppressor function, as reported in the Sample 5 column of the variant classification report table for the pool of 60 samples (FIG. 8b).

Overall, in the experiment the proposed method allowed us to identify 67 SNPs, 33 INDELs and 3 intragenic germline CNVs, which could explain the underlying genetic basis of the disease. Inferring sample purity, further allowed us to identify variant origin (i.e., germline vs. somatic) and perform LOH detection. Together with variant annotation information obtained from public databases to identify likely pathogenic variants, these results allowed us the establish the gene mutation status of BRCA1, BRCA2 and TP53 in each individual sample. Amongst the 60 patients 35 analysed in our experiment, 18 biallelic pathogenic variants were identified in the BRCA1 gene (30%), 7 in the BRCA2 gene (11.6%) and 29 in the TP53 gene (48.3%). Moreover, in 20 samples, none of the genes that were 36 analysed carried biallelic pathogenic variants. We also observed that in the BRCA1/BRCA2 genes, biallelic pathogenic variants were in most cases germline-derived variants which underwent LOH while in the TP53 gene, they were in most cases somatic variants which underwent LOH. Overall, this analysis allowed us to identify 23 cases in which patients would likely benefit from a PARP inhibition therapy such as olaparib to treat their ovarian cancer tumour.

Other Embodiments and Applications

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

While exemplary embodiments and applications of the proposed methods have been described in relation with the targeted next generation sequencing genomic analysis of BRCA1, BRCA2 and TP53 genes, it will be apparent to those skilled in the art of bioinformatics that they also apply to the detection and classification of variants of other tumor suppressor or homologous repair genes such as for instance ATM, CHEK1, CHEK2, BARD1, BRIP1, RAD51C, RAD51D, FAM175A, MRE11A, NBN, PALB2, APC, DCC, DF1, NF2, PTEN, Rb, VHL, WT1, PP2A, LKB1, or INK4a/ARF, and others which may be identified in the future as the scientific oncogenomics knowledge develops.

As will be apparent to those skilled in the art of digital data communications, the methods described herein may be indifferently applied to various data structures such as data files or data streams. The terms "data", "data structures", "data fields", "file", or "stream" may thus be used indifferently throughout this specification.

As will be apparent to those skilled in the art statistics, the methods described herein may be indifferently applied to various statistical methods such as probability representations and statistical measurements. The terms "distribution", "likelihood", "probability" may thus be used indifferently throughout this specification.

Although the detailed description above contains many specific details, these should not be construed as limiting the scope of the embodiments but as merely providing illustrations of some of several embodiments.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, units, or mechanisms. Modules or units may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities.

Although an overview of the inventive subject matter has been described with reference to specific example embodiments, various modifications and changes may be made to these embodiments without departing from the broader spirit and scope of embodiments of the present invention. For example, various embodiments or features thereof may be mixed and matched or made optional by a person of ordinary skill in the art. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are believed to be described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present invention as represented by the appended claims. The specification and drawings are, accordingly, to be regarded in an illustrative rather than a restrictive sense.

Finally, it is the applicant's intent that only claims that include the express language ""means for" or ""step for" be interpreted under 35 U.S.C. 112, paragraph 6. Claims that do not expressly include the phrase ""means for" or ""step for" are not to be interpreted under 35 U.S.C. 112, paragraph 6.

What is claimed is:

1. A method for treating cancer in a specified patient and identifying the presence of a chromosomal aberration in the tumor sample cells in at least one gene from the next generation sequencing data analysis of a pool of patient tumor samples only, with a variant classification data processor module, in which a combination of at least two genomic alterations have caused its biallelic loss of function,
the method of identifying the presence of chromosomal aberration comprising:
acquiring a variant calling information of the next generation sequencing of multiple patient tumor samples only, the variant calling information comprising for each patient a list of SNPs and INDELs genomic variants in at least two genes to be analyzed;
selecting, in the list of genomic variants, a set of putative germline heterozygous SNPs by comparing the list of genomic variants to a reference human genome variant database;
for each possible value sample purity value p, a sample purity p being a ratio of somatic DNA material in the overall FFPE sample, fitting a mixture model to the observed variant fraction distribution of said set in the variant calling data, the modeled variant fraction distribution values being calculated as a function of the sample purity p;
inferring an optimal sample purity $p_{optimal}$ as the possible sample purity p for which the mixture model best fits the observed variant fraction distribution of said set;
for each gene to be analyzed:
selecting, in the plurality of putative germline heterozygous SNPs, a subset of putative germline heterozygous SNPs located in the gene to be analyzed,
inferring the presence of a chromosomal aberration in the tumor sample cells by comparing, on at least said subset, the observed variant fraction distribution with the predicted variant fraction distribution for each possible chromosomal aberration, the predicted variant fraction distribution values being calculated as a function of the optimal sample purity $p_{optimal}$;

the method for treating cancer in the specified patient comprising:
- determining if cancer or precancerous lesions or benign tumors in the specified patient will be responsive to treatment with a PARP inhibitor, comprising:
  - detecting genomic alterations in BRCA1 and BRCA2 genes from the variant calling information with the method of identifying the presence of chromosomal aberration, and
  - if the specified patient sample cells carry a biallelic genomic alteration in the BRCA1 gene or in the BRCA2 gene, then determining that the specified patient cancer will respond to treatment with the PARP inhibitor; and
- treating the cancer in the specified patient with the PARP inhibitor if the cancer or precancerous lesions or benign tumors in the specified patient have been determined responsive to treatment with the PARP inhibitor.

2. The method of claim 1, wherein it further comprises: identifying if a combination of at least two genomic alterations have caused the biallelic loss of function of the gene in the tumor sample cells, the genomic alterations comprising SNPs, INDELs or chromosomal aberrations of likely pathogenicity in the gene.

3. The method of claim 1, wherein the variant fraction of each putative germline heterozygous SNP is compensated for capture-biases, by inferring and compensating the average loss a in capture efficiency due to the presence of a SNP in the tumor samples as the value a for which the compensated variant fraction distribution of all putative germline heterozygous SNP across all samples is maximally symmetric around 50%.

4. The method of claim 1, wherein a possible chromosomal aberration in the tumor cells is copy-neutral loss-of-heterozygosity.

5. The method of claim 1, wherein a possible chromosomal aberration in the tumor cells is the deletion of one allele.

6. The method of claim 1, wherein a possible chromosomal aberration in the tumor cells is the duplication of one allele.

7. The method of claim 1, wherein the mixture model is fitted to the data by minimizing a cost function based on the root mean squared error (RMSE) between the observed and the theoretical variant fraction expected for the most likely chromosomal aberration.

8. The method of claim 1, wherein inferring chromosomal aberrations comprises minimizing the root mean squared error (RMSE) between the observed variant fraction and the theoretical variant fractions expected for a plurality of chromosomal aberrations.

9. The method of claim 1, wherein estimating sample purity comprises fitting a mixture Model with mixture components corresponding to the different possible chromosomal aberrations using the Expectation-Maximization algorithm.

10. The method of claim 1, wherein estimating sample purity comprises fitting a mixture Model with mixture components corresponding to the different possible chromosomal aberrations using a Markov-Chain Monte-Carlo sampling algorithm.

11. The method of claim 9, wherein inferring the gene chromosomal aberrations comprises applying Mixture Model Classifiers.

12. The method of claim 1, further comprising detecting germline copy number variants (CNVs) in accordance with a Hidden Markov Model.

13. The method of claim 1, further comprising reporting to the end user whether the detected alterations are biallelic, for each gene in each sequenced patient tumor sample.

14. The method of claim 1, wherein a least one of the genes to be analyzed is a tumor suppressor gene.

15. The method of claim 1, wherein at least one of the genes to be analyzed is ATM, CHEK1, CHEK2, BARD1, BRCA1, BRCA2, BRIP1, RAD51C, RAD51D, FAM175A, MRE11A, NBN, PALB2, TP53, APC, DCC, DF1, NF2, PTEN, Rb, VHL, WT1, PP2A, LKB1, or INK4a/ARF.

16. The method of claim 1, wherein the PARP inhibitor is olaparib.

* * * * *